US012690807B2

(12) United States Patent
Mongia et al.

(10) Patent No.: US 12,690,807 B2
(45) Date of Patent: Jul. 28, 2026

(54) SYSTEMS AND METHODS FOR ANESTHESIA PHASE DETECTION

(71) Applicant: GE Precision Healthcare LLC, Waukesha, WI (US)

(72) Inventors: Aanchal Mongia, Bengaluru (IN); Sanjay Kumar NT, Bengaluru (IN); Abhijit Patil, Bengaluru (IN); John D. Page, Madison, WI (US); Sai Sudha, Bengaluru (IN); Sandeep S. Kurup, Bengaluru (IN); Badari Prasad Kg, Bengaluru (IN); Andrea Vitagliano, Madison, WI (US); Tom Häggblom, Vantaa (FI)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 329 days.

(21) Appl. No.: 18/458,825

(22) Filed: Aug. 30, 2023

(65) Prior Publication Data

US 2025/0072826 A1     Mar. 6, 2025

(51) Int. Cl.
    *A61B 5/00*        (2006.01)
    *A61B 5/08*        (2006.01)
    *G16H 40/20*       (2018.01)
(52) U.S. Cl.
    CPC .......... *A61B 5/4821* (2013.01); *A61B 5/0004* (2013.01); *A61B 5/0816* (2013.01);
                              (Continued)
(58) Field of Classification Search
    CPC ... A61B 5/4821; A61B 5/0004; A61B 5/0816; A61B 5/7282; A61B 5/7435; A61B 5/1106; G16H 40/20
    See application file for complete search history.

(56) References Cited

U.S. PATENT DOCUMENTS 5,522,387 A     6/1996 Simons
7,925,338 B2    4/2011 Huiku
                (Continued)

FOREIGN PATENT DOCUMENTS

CA        2934922 C   *   3/2023   ............. G16H 40/67
CN     107072737 A       8/2017
                (Continued)

OTHER PUBLICATIONS

Sebastiao, R. et al., Contributions to an advisory system for changes detection in depth of anesthesia signals, ResearchGate Website, Available Online at https://www.researchgate.net/publication/228485313_Contributions_to_an_advisory_system_for_changes_detection_in_depth_of_anesthesia_signals, Available as Early as Jan. 2011, 11 pages.
                (Continued)

*Primary Examiner* — Carl H Layno
*Assistant Examiner* — Heidi A Hilsmier
(74) *Attorney, Agent, or Firm* — McCoy Russell LLP

(57)         ABSTRACT

Systems are provided for perioperative care. In an example, a system includes one or more processors and memory storing instructions executable by the one or more processors to output a graphical user interface (GUI) including a first visual representation of a default or previously-determined phase of anesthesia delivery for a patient; receive a plurality of monitoring parameters of the patient over an observation window, at least a portion of the plurality of monitoring parameters obtained from an anesthesia delivery machine; identify, by applying a selected set of rules to the plurality of monitoring parameters, whether an event signaling a change to a new phase of anesthesia delivery for the patient is detected; based on the event being detected, update the GUI to display a second visual representation of the new
                (Continued)

phase; and based on the event not being detected, maintain the first visual representation on the GUI.

19 Claims, 11 Drawing Sheets

(52) U.S. Cl.
CPC .......... *A61B 5/7282* (2013.01); *A61B 5/7435* (2013.01); *G16H 40/20* (2018.01)

(56) References Cited

U.S. PATENT DOCUMENTS

| | | | |
|---|---|---|---|
| 9,826,931 B2 * | 11/2017 | Franz | .................... A61B 5/0205 |
| 11,317,858 B2 | 5/2022 | Tang et al. | |
| 2015/0150519 A1 * | 6/2015 | Glenn | ................. G06F 3/04847 |
| | | | 715/771 |
| 2016/0275268 A1 * | 9/2016 | Jones | ..................... G16H 10/20 |
| 2020/0315525 A1 | 10/2020 | Luo et al. | |
| 2021/0059616 A1 * | 3/2021 | Abrol | ................... A61B 5/7435 |
| 2021/0375446 A1 | 12/2021 | Page | |

FOREIGN PATENT DOCUMENTS

| | | | | |
|---|---|---|---|---|
| EP | 4184518 A1 | 5/2023 | | |
| WO | WO-2024149644 A1 * | 7/2024 | ............. | A61B 5/742 |
| WO | WO-2024263879 A1 * | 12/2024 | ............. | A61B 5/725 |

OTHER PUBLICATIONS

Gu, Y. et al., "Use of Multiple EEG Features and Artificial Neural Network to Monitor the Depth of Anesthesia," Sensors(Basel), vol. 19, No. 11, Jun. 2011, 12 pages.
Sebastiao, R. et al., "Real-time algorithm for changes detection in depth of anesthesia signals," Evolving Systems, vol. 3, Sep. 18, 2012, 10 pages.
Safavi, K. et al., "Remote Surveillance Technologies: Realizing the Aim of Right Patient, Right Data, Right Time," Anesthesia and Analgesia, vol. 129, No. 3, Sep. 2019, 9 pages.
Hashimoto, D. et al., "Artificial Intelligence in Anesthesiology: Current Techniques, Clinical Applications, and Limitations," Anesthesiology, vol. 132, No. 2, Feb. 2020, 16 pages.
EP application 24194148.3 filed Aug. 12, 2024—extended Search Report issued Jan. 29, 2025; 10 pages.
EP application 24194148.3 filed Aug. 12, 2024—Examination Report issued Jan. 2, 2026; 9 pages.
Schubert A U et al: "A fuzzy system for regulation of the analgesic remifentanil during general anaesthesia", Control and Automation, 2008 16TH Mediterranean Conference On, IEEE, Piscataway, NJ, USA, Jun. 25, 2008 (Jun. 25, 2008), pp. 1634-1639, XP031308501, ISBN: 978-1-4244-2504-4.

* cited by examiner

FIG. 4

SYSTEMS AND METHODS FOR ANESTHESIA PHASE DETECTION

FIELD

Embodiments of the subject matter disclosed herein relate to patient monitoring during perioperative care, and more specifically to automatic detection of patient anesthesia phase.

BACKGROUND

Certain medical procedures, such as surgery, may require various sub-procedures to be performed to prep the patient for surgery, maintain the patient in a certain condition during surgery (e.g., anesthetized), and help the patient recover after surgery. Such sub-procedures that are performed in support of a main procedure may be referred to as perioperative care. For a medical facility with multiple operating rooms, for example, monitoring of perioperative care may allow care providers and administrators to effectively manage resources of the medical facility, such as scheduling and preparation of patients for surgery.

BRIEF DESCRIPTION

In one embodiment, a system includes one or more processors and memory storing instructions executable by the one or more processors to output, for display on a display device, a graphical user interface (GUI) including a first visual representation of a default or previously-determined phase of anesthesia delivery for a patient; receive a plurality of monitoring parameters of the patient over an observation window, at least a portion of the plurality of monitoring parameters obtained from an anesthesia delivery machine; identify, by applying a selected set of rules to the plurality of monitoring parameters, whether an event signaling a change to a new phase of anesthesia delivery for the patient is detected, wherein the event is one of case start, induction start, induction end, emergence start, and case end; based on the event being detected, update the GUI to display a second visual representation of the new phase; and based on the event not being detected, maintain the first visual representation on the GUI.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 4 schematically shows example patient monitoring parameters that may be evaluated to detect an event signaling a change in anesthesia phase.

DETAILED DESCRIPTION

Figure 1:
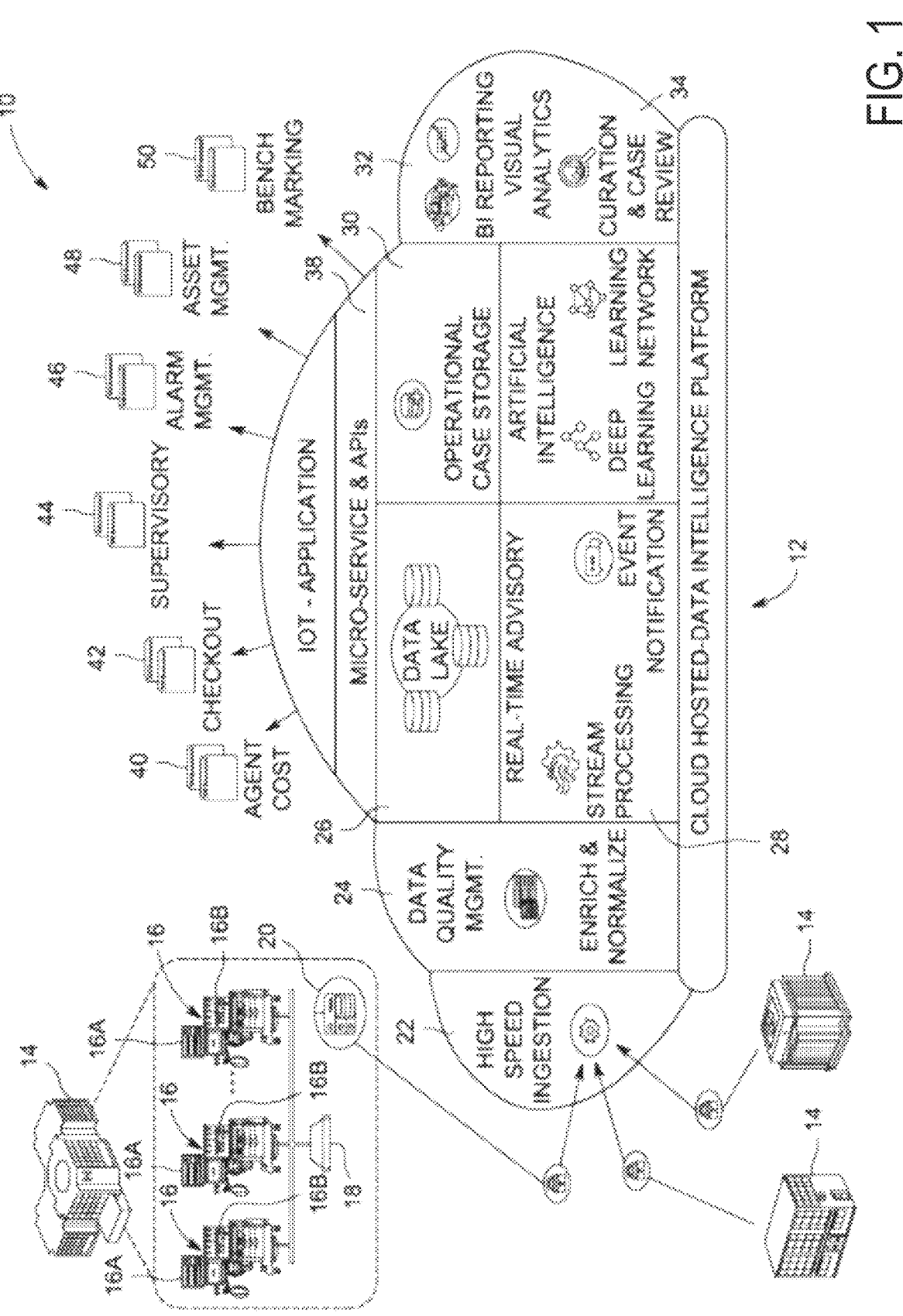
FIGS. 1 and 2 schematically show an example system for perioperative care and supervision configured to automatically detect anesthesia phase.

Embodiments of systems and methods as disclosed herein operate to facilitate perioperative care for a plurality of patients. To facilitate the perioperative care and supervision described herein, the systems and methods as disclosed herein collect and process medical device data. In particular, the medical device data may be processed in order to identify, for one or more patients being monitored, a current phase of anesthesia delivery. The process of delivering anesthesia may be classified into stages based on key events/timepoints. In particular, the process of anesthesia delivery may be classified based on the start of the process (referred to as case start (CS)), the start of induction (induction start (IS)), the end of induction (induction end (IE)), which is also the same as the start of maintenance (maintenance start (MS)), the start of emergence (emergence start (SE), which is also the same as the end of maintenance (maintenance end (ME)), and the end of the process (referred to as case end (CE)). Generally, induction refers to the transition from the patient being awake to being in an anesthetized state, maintenance refers to the maintenance of the patient in the anesthetized state, and emergence refers to when anesthesia is no longer needed and the agents administered during the maintenance phase can be switched off.

The current phase of anesthesia delivery may be displayed to one or more users outside the operating room (e.g., a supervising anesthesiologist, an administrator) via a visual dashboard (e.g., graphical user interface). In some examples, the visual dashboard may be displayed via a supervisory application that, in some examples, also facilitates presentation of the medical device data in real-time or near real-time via one or more graphical user interfaces that may be displayed on device(s) of the users, such as a mobile device (e.g., smart phone, tablet, wearable). The supervisory application may facilitate display of medical device data, including physiological data and medical device setting/ parameter data, for a plurality of patients and for a plurality of different patient monitoring parameters to the users. The displayed medical device data for the plurality of patients may be displayed simultaneously in a multi-patient graphical user interface (GUI), which may allow the users to easily monitor patient status for each patient, even if the user is located away from the patient(s).

The supervisory application may also monitor patient status, via the medical device data, and may output various notifications, such as alarms, when patient anesthesia phase changes or when a patient has been in a certain phase of anesthesia for longer than a threshold duration.

The visual dashboard and functions of the supervisory application described above may allow for a single supervising care provider and/or administrator to simultaneously monitor multiple patients during respective medical procedures, such as surgery. While each patient may be attended to by multiple care providers during the medical procedure, such as one or more surgeons, nurses, medical technicians, etc., certain supervising care providers, such as anesthesiologists, may attend to multiple patients at once and may oversee a plurality of subordinate care providers, such as nurse anesthesiologists. As the number of subordinate care providers increases relative to the number of supervising care providers, and as medical procedures become more complex, the need for a supervising care provider to be able to monitor patients and oversee subordinate care providers remotely has increased. For example, a supervising anesthesiologist may be scheduled to initiate and monitor an induction phase of anesthesia for a first patient. However, the supervising anesthesiologist may also be attending to six other patients that are in the maintenance and emergence phases of anesthesia. The visual dashboard may notify the supervising anesthesiologist of a relatively long emergence phase for a particular patient, which may indicate delayed recovery due to anesthetic causes (deep anesthesia), which may allow for additional monitoring or action from an anesthesiologist. In doing so, patient care may be improved.

Further, the automatic, real-time detection of the current anesthesia phase for each of a plurality of patients may be beneficial for resource utilization at the hospital/medical facility. For example, displaying a summarization of which operating rooms (OR) have patients that are in which anesthesia phases at a given time point may help the hospital administration make correct decisions, such as estimating the wait times for each OR, deciding on staffing requirements, next surgery preparations, etc. As another example, a relatively long time lag between a case start and induction start could indicate a delay in progress of the case due to unavailability of equipment and nurses/anesthesiologists, etc., which may be notified to the hospital administration. Additionally, large time lags between emergence end and case end may indicate logistic issues (patient waiting on bed, lack of manpower). At the same time, in such cases, notifying that the patient is ready for transfer using the patient's anesthesia machine parameters or monitor parameters allows more preparation time for the next patient in queue for entry into the OR.

As used herein, medical device data includes physiological data (also referred to as patient monitoring data) of a patient that is acquired from a medical device and machine data collected internally from the medical device itself. Machine data may include alarms, device status, settings, messages, and measured operational data. Machine data may further include settings and values that represent specific actions taken with the medical device for example, in response to automated controls or due to clinician inputs. For example, in an anesthesia delivery machine, this may include changes to oxygen and/or anesthetic agent concentrations. The machine data may further include clinical and/or technical alarms initiated by the medical device or device diagnostic information. Still further examples of the machine data include proactive or predictive service alerts from the medical device, maintenance checkout information, and/or processor clock cycle signals or power signals or other operational signals from various components of the medical device indicative that the medical device is turned on, in use, in operation, held in a stand by condition, or turned off.

The medical device data can be collected in time series format as provided from the medical devices themselves. As used herein, the time series format of the medical device data can include waveforms, binary data, numeric data, and/or textual data in a time series format. Embodiments of the systems and methods as disclosed herein receive the medical device data from the medical devices at a frequency similar to the frequency at which it is produced by the medical devices. In embodiments, this increased velocity of the received data and the monitoring and analysis of medical device machine data can enable improved monitoring systems and methods as disclosed herein. As described in further detail herein, embodiments of systems and methods support high speed data ingestion, enrichment, normalization, and data curation of the medical device data. The medical device data can undergo real time analysis and further enrichment of the data with event detection and notation.

Figure 2:
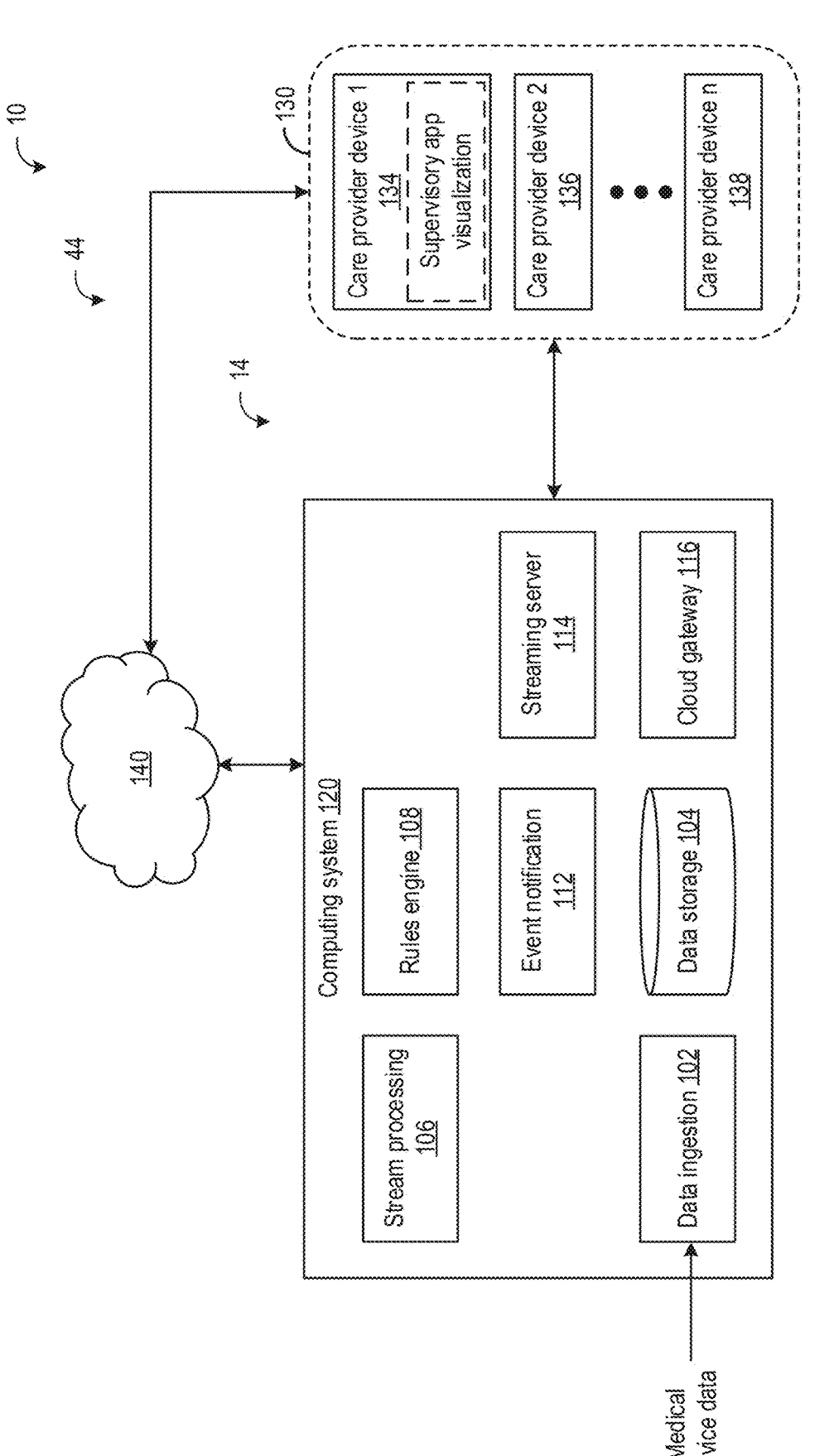

FIGS. 1 and 2 depict an exemplary embodiment of a system 10 for perioperative care and supervision that may be configured to automatically detect and report current anesthesia phase for a plurality of patients. Referring first to FIG. 1, system 10 includes a medical device data (MDD) processing system 12. The MDD processing system 12 can be implemented in a variety of hardware and/or software implementations and it should be noted that such implementations are not considered to be limiting. For example, it is contemplated that any or all of the MDD processing system 12 may be embodied exclusively in hardware, exclusively in software, exclusively in firmware or in any combination of hardware, software, and/or firmware. While the following describes exemplary methods and systems, the examples provided herein are not the only way to implement such methods and systems.

In embodiments that cover an entirely software and/or firmware implementation, in any embodiment, at least one of the elements is hereby expressly defined to include a tangible and non-transient computer readable medium. As used herein, the term tangible computer readable medium is expressly defined to include any type of computer readable storage and to exclude propagating signals. Additionally or alternatively, the example methods and systems may be implemented using coded instruction (e.g., computer readable instructions) stored on a non-transitory computer readable medium such as a flash memory, a read-only memory (ROM) a random-access memory (RAM), a cache, or any other storage media in which information is stored for any duration (e.g. for extended period time periods, permanently, brief instances, for temporarily buffering, and/or for caching of the information). As used herein, the term non-transitory computer readable medium is expressly defined to include any type of computer readable medium and to exclude propagating signals.

In exemplary and non-limiting embodiments of the medical device data processing system 12, the MDD processing system 12 is implemented by one or more networked processors or computing devices. Processing system 12 may be implemented in a cloud computing platform and/or infrastructure. Memory and processors as referred to herein can be standalone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be standalone or as part of a computing device. Examples of computer memory may include, but are not limited to RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

The MDD processing system 12 is communicatively connected to at least one hospital network 14. Such communicative connections as well as the hospital network itself may include, but are not limited to, a wide area network (WAN); a local area network (LAN); the internet; wired or wireless (e.g. optical, Bluetooth, radio frequency (RF)) network; a cloud-based computer infrastructure of computers, routers, servers, gateways, etc.; or any combination thereof associated therewith that allows the system or portions thereof to communicate with one or more computing devices.

The hospital network 14 may exemplarily be a network associated with a portion of a hospital, for example a surgery unit or department of a hospital, or may be more broadly located across medical devices of an entire hospital. It further will be recognized that while some embodiments and implementations of the systems and methods as disclosed herein may seek to operate on a single hospital or unit of a hospital, still other embodiments may connect a plurality of hospital networks, including hospitals currently owned or operated or otherwise affiliated with one another. In still further embodiments, while individual hospitals or groups of hospitals may use the MDD processing system 12, the MDD processing system 12 may receive and process information from a plurality of hospital networks including those unaffiliated with one another at the same time.

As depicted in FIG. 1, the hospital network 14 includes a plurality of medical devices 16. The medical devices 16 may include physiological monitoring devices 16a as well as patient therapy devices 16b. Physiological monitoring devices 16a may include, but are not limited to, patient monitors (e.g., heart rate monitors, blood pressure and/or oxygenation monitors, respiration monitors), ECG monitors, EEG monitors, or EMG monitors. An example of an anesthesia delivery machine will be used for discussion purposes as the medical device, and more specifically as the patient therapy device 16b, although it will be recognized by a person of ordinary skill in the art that other devices, including but not limited to patient respiratory assistance devices or dialysis machines, may be further non-limiting examples of patient therapy devices. However, it will be recognized that therapy devices may also include capabilities to not only deliver patient therapy, but also to measure physiological parameters of a patient. For example, embodiments of anesthesia delivery machines may include gas analysis modules operable to measure gas concentrations expired by the patient. In some embodiments, imaging devices, including but not limited to X-ray, CT, MRI, and ultrasound devices, may be examples of medical devices 16 as contemplated within the present disclosure. Still further examples of medical devices may include video and/or audio recording devices.

In some examples, a limited version of the MDD processing system 12 as described herein may be implemented locally, for example as an anesthesia delivery management system 18. In such an embodiment, the anesthesia delivery management system 18 may operate to collect medical device data from a plurality of anesthesia delivery machines inter alia to monitor anesthesia agent use between anesthesia delivery machines and across procedures performed by the anesthesia delivery machines in an effort to visualize anesthetic agent consumption and use as well as to quantify, monitor, and evaluate trends across all of the anesthesia delivery machines in the hospital or surgical unit, in addition to the automatic detection of anesthesia phase disclosed herein.

The medical devices 16 may be communicatively connected to one or more edge devices, such as edge device 20. Edge device 20 may exemplarily be an edge processing device, cloud processing device, or internet gateway. The edge device 20 may include an internet of things (IOT) gateway which facilitates a secure communications link between the medical devices 16 at the hospital network 14 with the servers, processors, and computer readable media implementing the MDD processing system 12. In some embodiments, the edge device 20 may communicate directly with one or more of the medical devices 16, or may communicate with the medical devices 16 through an intermediate network, for example, the anesthesia delivery management system 18 or another medical device data system or network.

The edge device 20 receives the medical device data as time series data for any of the medical device data available from the medical devices. As noted above, the data streams of medical device data (e.g., machine data, monitored patient physiological parameter data) are available in time series format as acquired from the medical devices and may include, but are not limited to time series information of alarms, device status, device settings, messages, and measured data. In embodiments, the medical devices may be equipped with sensors that improve the self-awareness of the medical device, e.g. sensors that monitor the function, inputs and/or outputs of various components of the medical device itself. Many such sensors are already incorporated into medical devices such as to measure compressor speeds and/or cycle times, internal pressures, voltages, clock speeds, or temperatures, or other sensors as will be recognized by a person of ordinary skill in the art or as disclosed in further detail herein.

The edge device 20 encrypts the time series formatted data and the encrypted data is transmitted using wired and/or wireless communication techniques for encrypted data to the server, processors, and data storage carrying out the MDD processing system 12. The edge device 20 continuously transmits de-identified medical device data in time series format over an encrypted communication channel to a high speed data ingestion module 22 of the MDD processing system 12. While the embodiment described herein may reference de-identified data, it will be recognized that other embodiments may use patient-identified data with appropriate considerations taken for handling patient data. The high speed data ingestion module 22 takes in the real time streams of medical device data. The data ingestion can be performed in an automated fashion and can preprocess the received streams of real time data in the time series for later processing by the MDD processing system 12. The high speed data ingestion module 22 can receive concurrent data streams from multiple connected devices across multiple sites at a high incoming velocity, for example at or near the frequency at which medical devices can output data. In some embodiments, the high speed data ingestion module 22 is scalable to continue to ingest increased bandwidth of medical device data without significant decrease in ingestion speeds.

The high speed data ingestion module 22 takes the time series medical device data from the medical devices of one or more hospital networks and formats it for further processing by a data quality management module 24. In exemplary and non-limiting embodiments, the high speed data ingestion module 22 supports open standard such as ASTMF 2761 or integrated clinical environmental (ICE). The data quality management module 24 may normalize, enrich, and tag the data streams without negatively impacting data latency. In a healthcare environment, a variety of healthcare information products and/or systems may be used to provide medical services, collect medical data, conduct medical exams, etc. However, many healthcare information systems operate using various messaging standards (e.g., Health Level 7 International (HL7 V2.x/v3), Clinical Document Architecture/Continuity Of Care Document (CDA/CCD), American Society for Testing Materials (ASTM), Digital Imaging and Communications in Medicine (DICOM), etc.)) and various standards and/or protocols (e.g., cross-enterprise document sharing (XDS.A/B) cross-enterprise document media interchange (XDM) cross-enterprise document reliable interchange (XDR), patient identifier cross-referencing/patient demographics query (PIX/PDQ) patient administration management (PAM), query for existing data (QED), national counsel for prescription drug programs (NCPDP), etc.)) that make system integration and/or communication more difficult. Thus, normalization may include reformatting of medical data to a consistent or compatible format for use within the MDD processing system 12. In one embodiment, the medical device data may be normalized into the ISO/IEEE 11073-10101 nomenclature and its extensions. In a still further embodiment, the data quality management module 24 can normalize the streams of incoming time series data by converting units of measure. The data quality management module 24 can further operate to identify and tag various types of medical device data, locations from which the medical device data was received, or time series data streams originating from the same medical device. These tags can be used as further detailed herein to identify and analyze groups of streams of time series data.

In some embodiments, the data quality management module 24 normalizes the received incoming data by transforming and/or translating the clinical data streamed from the source healthcare system or device into a canonical data model with associated metadata. The processed medical device data is stored in a data lake 26 which is exemplarily implemented in computer readable storage embodying capability to store terabytes of data. The data lake 26 is a long-term computer storage repository that holds large amounts of raw data in a native format until the data is needed. The native format may include the time series data from the medical devices which may be in waveform or binary format, audio data, image data, and/or video data. In embodiments, this can help to facilitate the ingestion of the data that may not be processed in real time but may still be taken in in real time or near real time and instead stored in the data lake until further needed. This may be facilitated by identifying particular data streams and limiting the processing of those data streams, for example by the data quality management module 24, if it is known at that time that such data stream is not being used in real time analysis. In an exemplary embodiment, the data quality management module 24 may not convert the data to a canonical data model but may still attempt to tag, enrich, or index the data to facilitate later retrieval of that data in a standardized way from the data lake 26.

In a still further embodiment, portions of the data that are stored in the data lake 26 may also be additionally stored in a graph database which may be a separate database residing on the same computer readable storage, or may be embodied on separate computer readable storage from the data lake 26. The graph database may receive the data streams of which it is known that the system may analyze trends in that data stream. The graph database may store the streams of data in a time series format in a way that facilitates trending of the data over time and appending the data with events either identified in the data itself, in one or more of the other data streams, or received by the system from an external source. These events may include, but are not limited to, medical device or clinician actions, clinical events, situations, or complications that arise during the medical procedure. The graph database may later be used by a clinician or technician to identify further relationships between trends and the data streams with other analysis as disclosed herein.

At the same time that the data is stored in the data lake 26, the enriched and normalized medical device data may be provided to a stream processing engine 28. The stream processing engine 28 identifies cases and events in the time series streams of medical device data. Identified clinical cases may be stored in an operational case database 30. Clinical cases may exemplarily include surgical and intensive care unit (ICU) cases. The clinical cases may be identified by the medical device used and the timing of the medical data in the time series of the medical device data. For example, a time series of medical device data from an anesthesia delivery machine showing a change in status turning the machine on and followed by changes to device settings and delivery and/or consumption of anesthetic agent all indicate that a clinical case has begun or is ongoing.

As noted above, the streams of time series medical device data originating from the same medical device or from the same location in a hospital may be tagged or otherwise identified as being related. These tags can be used to simultaneously analyze related data streams or combine analysis of related data streams to identify clinical cases. For example, a device status data stream analysis may be combined with a user input data stream, device setting data stream, and operational data streams to identify when the device is used and how it is used in the clinical case. This information may help to distinguish between a maintenance or checkout of the medical device by a technician from the use of the device for clinical case.

The analysis of the data streams of multiple medical devices, particularly those identified as being related or co-located may further be used to identify clinical cases. For example, coordinated or similar actions in data streams of an anesthesia delivery device and a related patient monitoring device, and/or respiratory support device and/or imaging device, etc., may further be used to identify that these devices are being used together for a clinical case. In still further embodiments, the streaming time series medical device data may be combined with information regarding scheduled clinical cases to help to further identify when and how the medical devices are used during clinical cases.

In embodiments, knowledge of a scheduled use of the medical device (e.g. anesthesia delivery machine) can be used to further identify clinical cases in the streams of medical device data. For example, input or received knowledge regarding a type and time of a scheduled procedure may help to identify the start and end of the clinical case in particular streams of medical device machine data. In an embodiment, a known schedule of use for the medical device may help to identify clinical cases from maintenance or calibration actions which may similarly require powering up and at least partial operation of the medical device.

The medical device data associated with the actions by the anesthesia delivery machine and/or other medical devices during the identified clinical case may be stored in the operational case database 30. In an example, the identification of the clinical case is stored along with the other time series streams of medical device data from that anesthesia delivery machine as well as time series streams of medical device data from any physiological monitors and/or other medical devices associated with the use of that anesthesia delivery machine. In another exemplary embodiment as described in further detail, a clinical case summary with links or identifiers to the associated time series medical device data stored in the data lake 26 can be created and stored in the operational case database 30.

In an embodiment, prior to storing the clinical cases in the clinical case database 30, the clinical cases may be classified or profiled which is a technique used for data curation. The profiling of the clinical cases may be based upon, in part, the information in the clinical case summary. The profiling may be used to group the clinical cases into groups, for example normal cases, edge cases, and outlier cases. These determinations may be made in view of a comparison between the time series data in the clinical case against normal distributions of the same type of time series machine data in other similar clinical cases. Edge cases may be identified as borderline or ambiguous cases, not clearly defined as either normal or an outlier. In an embodiment, for a particular measured value or occurrence, a distribution of such occurrences may be used to establish normal, edge, and outlier cases. In an embodiment, a normal case may be within a standard deviation of a median value in the normal distribution while edge cases are between one and two standard deviations and outlier cases are greater than two standard deviations from the median. The categorized cases, as explained in further detail herein, for example, identified edge cases may be further investigated to create or improve event detection algorithms, rules for clinical decision support, alert algorithms, and predictive algorithms.

The stream processing engine 28 also identifies events in the time series streams of medical device data, for example in the manners as described in further detail herein and presented in reporting and visual analytics tools 32 which exemplarily may be presented on a graphical display communicatively connected to the medical device data processing system 12.

Once clinical cases are stored in the operational case database 30, clinical cases may be reviewed manually by a clinician or technician using a curation and case review tool 34. The curation and case review tool 34 may be presented in a graphical user interface on a graphical display and further provide inputs exemplarily through the graphical user interface for the user or technician to curate or otherwise assess the clinical cases. This can be performed for investigative, educational, and data curation purposes.

The reporting and visual analytics tool 32 can present the detected events in a variety of channels of communication. For example, the detected events may be presented visually through graphical user interfaces and graphical displays. The detected events or notifications of the detected events can also be reported by communication of events/event notifications to wearable or mobile devices and presentation of medical device data and identified events in visual form in reports and/or dashboards presented in a graphical user interface on a graphical display, as will be explained in more detail below.

The results of the streaming analytics and event detection in the time series of medical device data may be provided to an application programming interface (API) 38 for use by application developers to provide monitoring, reporting, and/or control applications based upon the analyzed streams of medical device data. Such applications may operate through a computer operating system, a website browser, or operate on a mobile computing device or wearable computing device. Non-limiting examples of applications that may leverage the analysis of the time series medical device data include, but are not limited to, an anesthetic agent cost dashboard 40, a checkout dashboard 42, a supervisory application 44, an alarm management application 46, an asset management application 48, and a benchmarking application 50.

The agent cost dashboard 40 may present medical device data regarding anesthetic agent use across clinical cases as well as between anesthesia delivery machines within a hospital network or comparatively between hospital networks. By comparatively presenting this information, anesthetic agent use and behavioral changes can be understood and undertaken to promote efficient use of anesthetic agent.

The checkout dashboard 42 may assist in monitoring the inspection and maintenance of the monitored medical devices. Medical device data such as device status and settings, as well as messages and information in machine data, may provide insight into the inspection processes for maintaining medical devices at a hospital network. The checkout dashboard may identify maintenance and/or testing events in the streams of machine data and note these identified testing events against a testing schedule, requirement (e.g., daily), or other criterion.

The supervisory application 44 may be used by attending and/or supervising anesthesiologists to more efficiently manage remote personnel, nurse anesthetists, and/or other care providers simultaneously working across multiple locations or theatres. Additionally or alternatively, the supervisory application 44 may be used by ward or site administrators to more efficiently manage personnel, scheduling, equipment, and the like. The alarm management application 46 may report and present medical device data regarding alarm notifications and silences of alarm notifications in order to better understand and adjust alarms to improve signal to noise in alarm events and to reduce alarm fatigue by clinicians. Additional information about the supervisory application 44 is presented below.

The asset management applications 48 may present use, status, maintenance, and/or inspection information regarding medical devices (e.g. anesthesia delivery machines) or consumables used by medical devices, including components that may be frequently replaced, refilled, or refurbished during normal operation of the medical device (e.g. filters, absorbers). The benchmarking application 50 may provide further operational and quality performance across providers and/or organizations or in a comparative manner, for example, between hospital networks versus averages or between specific locations.

The supervisory application 44 allows for users (e.g., clinicians such as anesthesiologists, nurses, and other care providers as well as administrators) to view anesthesia delivery phase, ventilator, anesthesia, and vital parameters of a plurality of patients in different locations (e.g., in different operating rooms) on various workstations, smart phones, tablets, or other computing devices associated with the users. The supervisory application 44 may include a backend that is hosted on edge device 20 and/or MDD processing system 12 as dockers/micro services and may be rendered on a user's device (such as care provider device 134 shown in FIG. 2) using a suitable visualization platform.

FIG. 2 schematically shows example devices of system 10 via which supervisory application may be executed, including a computing system 120 in communication with a plurality of care provider devices 130 via hospital network 14 and/or via a separate network 140. The computing system 120 may be the edge device 20 and/or the MDD processing system 12 of FIG. 1.

As mentioned above, the computing system 120 receives the medical device data from the medical devices 16. The medical device data received by the computing system 120 may be ingested by a data ingestion module 102, which may be similar to ingestion module 22 of FIG. 1, and stored in data storage 104. Data storage 104 may be an ephemeral datastore where the received data is stored temporarily rather than persistently, or the data storage 104 may include long-term storage. Further, the received medical device data may be allocated to various micro services on the computing system 120 in order to carry out aspects of supervisory application 44, including a stream processing module 106, a rules engine 108, an event notification service 112, a streaming server 114, and a cloud gateway 116.

As explained above, the supervisory application 44 may be used by attending and/or supervising anesthesiologists to manage other care providers, such as nurse anesthesiologists and/or other subordinate care providers. The hospital/medical facility may rely on a relatively high supervision ratio (e.g., 4-10 subordinate care providers for each supervising anesthesiologist), which may increase the need for the supervising anesthesiologists to have high mobility among operating rooms while still overseeing all subordinate care providers and monitoring patient status for all procedures that may be simultaneously ongoing. The supervisory application 44 may facilitate this mobility and management by allowing supervising anesthesiologists to monitor patient status and communicate with subordinate care providers from a remote location. As will be explained in more detail below, the supervisory application 44 may present, via one or more graphical user interfaces displayed on a mobile or other device of a supervising anesthesiologist, patient monitoring parameters (e.g., ECG, heart rate, blood oxygenation) as determined from the received medical device data, procedure phase (e.g., case start, induction, maintenance, emergence, and case end), alarms, anesthesiology machine settings, and other relevant or selected information to a user (e.g., the supervising anesthesiologist and/or administrator). The processing and analysis of the time series streams of medical device data as described above in order to detect events relevant to identified cases (e.g., such as identifying a phase of anesthesia administration) may be utilized and the output of such processing and analysis may be provided to the supervisory application 44. The supervisory application 44 may provide determined values of specified patient monitoring parameters, indications of detected events, and other notifications as determined from the time series streams of medical device data to the user via the graphical user interfaces described herein.

For example, via the supervisory application 44, the user may toggle between graphical user interfaces that show limited information for a plurality of patients (a multi-patient GUI), including current procedure phase (e.g., anesthesia delivery phase), and more detailed information for a selected patient (a single patient GUI). The user may also view, via the supervisory application 44, trends of patient monitoring data, detailed alarm/notification information, insights, and/or other information. Further, the user may communicate with other care providers, such as a subordinate care provider that is in the room with a patient, via the supervisory application 44. The user may customize which patients/rooms to view, which patient monitoring parameters to view, which alarms to apply, and other parameters of the graphical user interfaces used to present the above-described information, such as a layout of each graphical user interface.

The graphical user interfaces that are generated via the supervisory application 44 may be displayed on one or more suitable display devices associated with a respective care provider device and/or medical facility administration device. As shown in FIG. 2, a plurality of care provider devices 130 may be included as part of hospital network 14, from a first care provider device 134, a second care provider device 136, and on up to an nth care provider device 138, and may be communicatively coupled to computing system 120 via hospital network 14. Each care provider device may include a processor, memory, communication module, user input device, display (e.g., screen or monitor), and/or other subsystems and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. The care provider devices may be located locally at the medical facility and substantially fixed in place (such as in a nurses station or in the room of a patient) and/or located locally or remotely from the medical facility and configured to move with the care provider (such as a care provider's mobile device).

When viewing graphical user interfaces generated via the supervisory application 44 via a display of a care provider device, a care provider may enter input (e.g., via the user input device, which may include a keyboard, mouse, microphone, touch screen, stylus, or other device) that may be processed by the care provider device and sent to computing system 120. In examples where the user input is a selection of a link or user interface control button of a graphical user interface, the user input may trigger progression to a desired view or state of the graphical user interface (e.g., trigger display of desired patient medical information), trigger updates to the configuration of the graphical user interface, trigger alarm, insight, and/or other notification settings to be saved, trigger changes to a machine (such as an anesthesia delivery machine), or other actions.

The devices disclosed herein, such as the care provider devices and/or aspects of the computing system 120, may each include a communication module, memory, and processor(s) to store and execute aspects of the supervisory application 44 as well as send and receive communications, graphical user interfaces, medical data, and other information.

Each communication module facilitates transmission of electronic data within and/or among one or more systems. Communication via the communication module can be implemented using one or more protocols. In some examples, communication via the communication module occurs according to one or more standards (e.g., Digital Imaging and Communications in Medicine (DICOM), Health Level Seven (HL7), ANSI X12N, etc.). The communication module can be a wired interface (e.g., a data bus, a Universal Serial Bus (USB) connection, etc.) and/or a wireless interface (e.g., radio frequency, infrared, near field communication (NFC), etc.). For example, a communication module may communicate via wired local area network (LAN), wireless LAN, wide area network (WAN), etc. using any past, present, or future communication protocol (e.g., BLUETOOTH®, USB 2.0, USB 3.0, etc.).

Each memory may include one or more data storage structures, such as optical memory devices, magnetic memory devices, or solid-state memory devices, for storing programs and routines executed by the processor(s) to carry out various functionalities disclosed herein. Memory may include any desired type of volatile and/or non-volatile memory such as, for example, static random access memory (SRAM), dynamic random access memory (DRAM), flash memory, read-only memory (ROM), etc. The processor(s) may be any suitable processor, processing unit, or micro-processor, for example. The processor(s) may be a multi-processor system, and, thus, may include one or more additional processors that are identical or similar to each other and that are communicatively coupled via an inter-connection bus.

As used herein, the terms "sensor," "system," "unit," or "module" may include a hardware and/or software system that operates to perform one or more functions. For example, a sensor, module, unit, or system may include a computer processor, controller, or other logic-based device that per-forms operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may repre-sent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more opera-tions described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, computing system 120 is shown in FIG. 2 as constituting a single entity, but it is to be understood that computing system 120 may be distributed across multiple devices, such as across multiple servers.

The supervisory application 44 may provide various data, notifications, and messages to the plurality of care provider devices 130. The data, notifications, and/or messages may include historical data, real-time medical device data (e.g., provided by streaming server 114), and notifications that may pushed to the plurality of care provider devices 130 from an event notification service 112.

As will be explained in more detail below, the supervisory application 44 may be visualized on a care provider device in the form of one or more graphical user interfaces. The one or more graphical user interfaces may be populated with real-time patient monitoring parameters, including a current phase of anesthesia delivery. In some examples, the one or more graphical user interfaces may further be populated with other real-time patient monitoring parameters, such as most-recently determined values or waveforms for heart rate, blood oxygen saturation, respiration rate, and so forth, obtained from the medical devices. When the medical device data is received by the computing system 120, some or all of the medical device data may be processed by stream processing module 106 and supplied to the streaming server 114, which may then supply the real-time patient monitoring parameter values and/or waveforms to a requesting care provider device. For example, when a user is viewing a patient-specific graphical user interface of the supervisory application 44 on care provider device 134, the graphical user interface may include tiles or other display areas where the most-recently determined values for selected patient monitoring parameters are displayed. The streaming server 114 may stream the most-recently determined values for the selected patient monitoring parameters to the care provider device 134, which may then populate the received values into the graphical user interface. The stream processing module 106 may include rule-based streaming analytics algorithms applying windowing functions (sliding, tum-bling, hopping, etc.) used for waveform analysis and event detection, thereby triggering alerts, detection of surgical phases, flow analysis, triaging algorithms, etc.

The determination of which patient monitoring parameter values to send to which care provider device may be based at least in part on data requests sent by the care provider devices to the computing system 120. The computing system 120 may include a representational state transfer (REST) server, for example, that may receive data requests from the care provider devices 130 and may respond to the data requests by commanding the streaming server 114 to stream selected medical device data to a requesting care provider device(s). The streaming server 114 may maintain a stateful session (e.g., WebSocket) with each client (e.g., the care provider devices). The medical device data may be adapted (transformed and filtered) before being streamed to the client devices.

The supervisory application 44 may generate and/or send various alarms and notifications based on the medical device data received from the various medical devices. The alarms may include threshold-based alarms, where a notification/ alarm is generated and output to one or more care provider devices in response to a patient monitoring parameter value meeting a predetermined condition relative to a threshold (e.g., an alarm may be generated and sent to a care provider device in response to a duration of an emergence phase for a particular patient exceeding a threshold duration). Com-puting system 120, via event notification service 112 and/or cloud gateway 116, may send a notification of the alarm to the care provider device of the care provider attending to the patient and/or to a care provider device of an administrator. For example, the alarms that are generated may be sent to the appropriate care provider device(s) directly via event noti-fication service 112 or via the cloud gateway 116, which may push the alarms (and other notifications that are generated by computing system 120, as explained in more detail below) to the appropriate care provider device(s), even when the supervisory application 44 is in an unlaunched state on the care provider device(s).

The rules engine 108 may include resources (e.g., memory and processors) of the computing system 120 allocated to store and apply sets of anesthesia event detec-tion rules, which may be applied to the medical device data in order to automatically determine whether an event sig-naling a change in anesthesia phase has occurred, for each of a plurality of patients, in real-time or near real-time. As mentioned above, the current phase of anesthesia delivery may be identified based on a set of events (CS, IS, IE/MS, ES/ME, and CE). To correctly detect the above events, sliding windows of time-series medical device data (e.g., anesthesia delivery machine data and optionally patient monitor parameters) are collected as input and rule-based logic is deployed to detect each event in real-time. A previous state/event need not be maintained to support a state-less architecture (with low input/output cost). Each input parameter can come at a variable frequency which can further be interpolated in the module. Patient case can be parsed with a given window size (preferably small, e.g., 1 minute) with a slide (e.g., 1 second). In other words, for each machine and/or monitoring parameter, a time-aligned window of data (e.g., a minute of data) may be collected and the sets of event detection rules may be applied on each window of data to identify if an event is detected, which may be repeated with new windows of data at a given frequency (e.g., each second). Additional details about the event detection rules and machine and monitor parameters that may be evaluated to determine the current phase are provided below.

Figure 8:
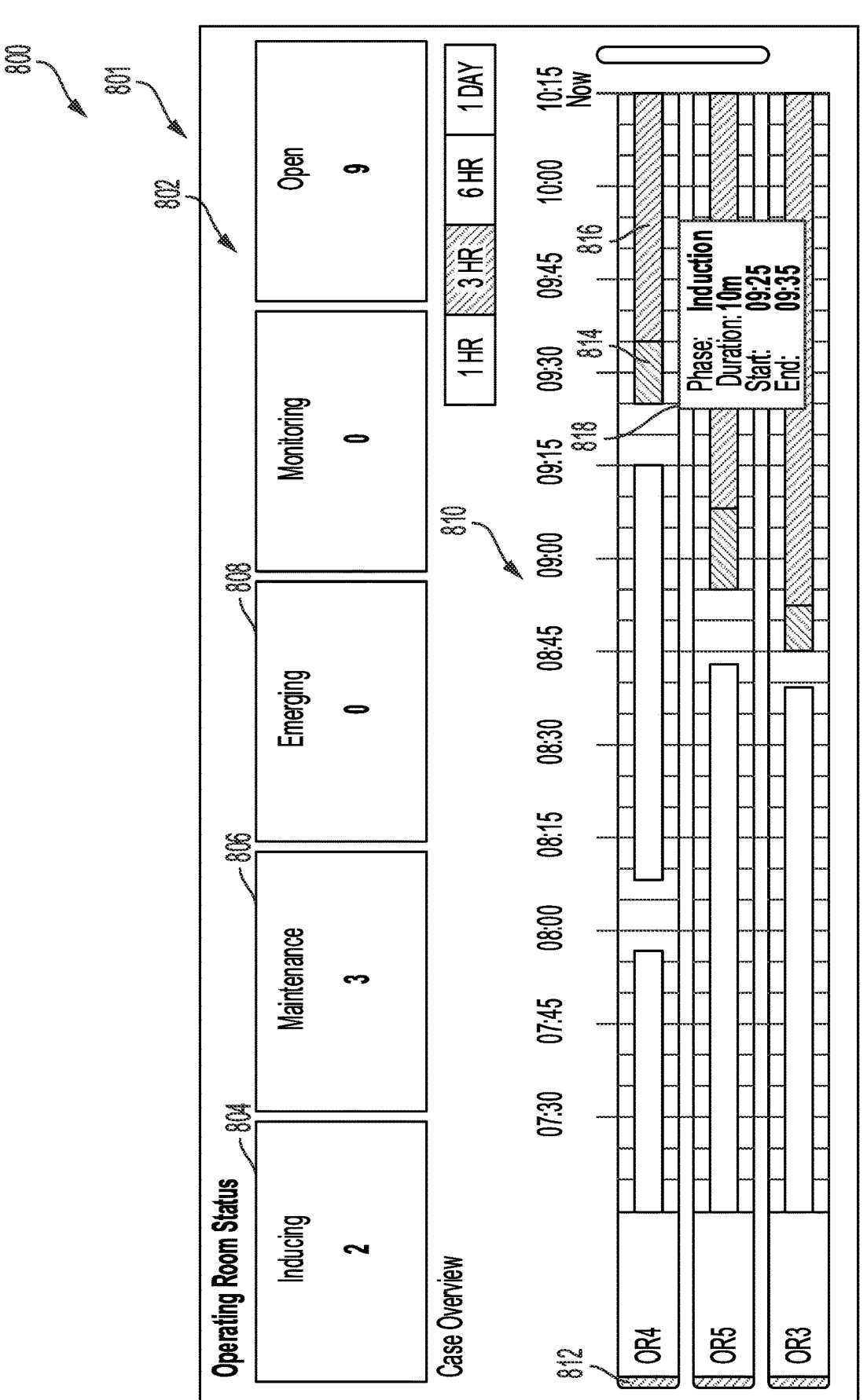
FIGS. 8-10 show an example graphical user interface depicting anesthesia phase for a plurality of patients.
Figure 9:
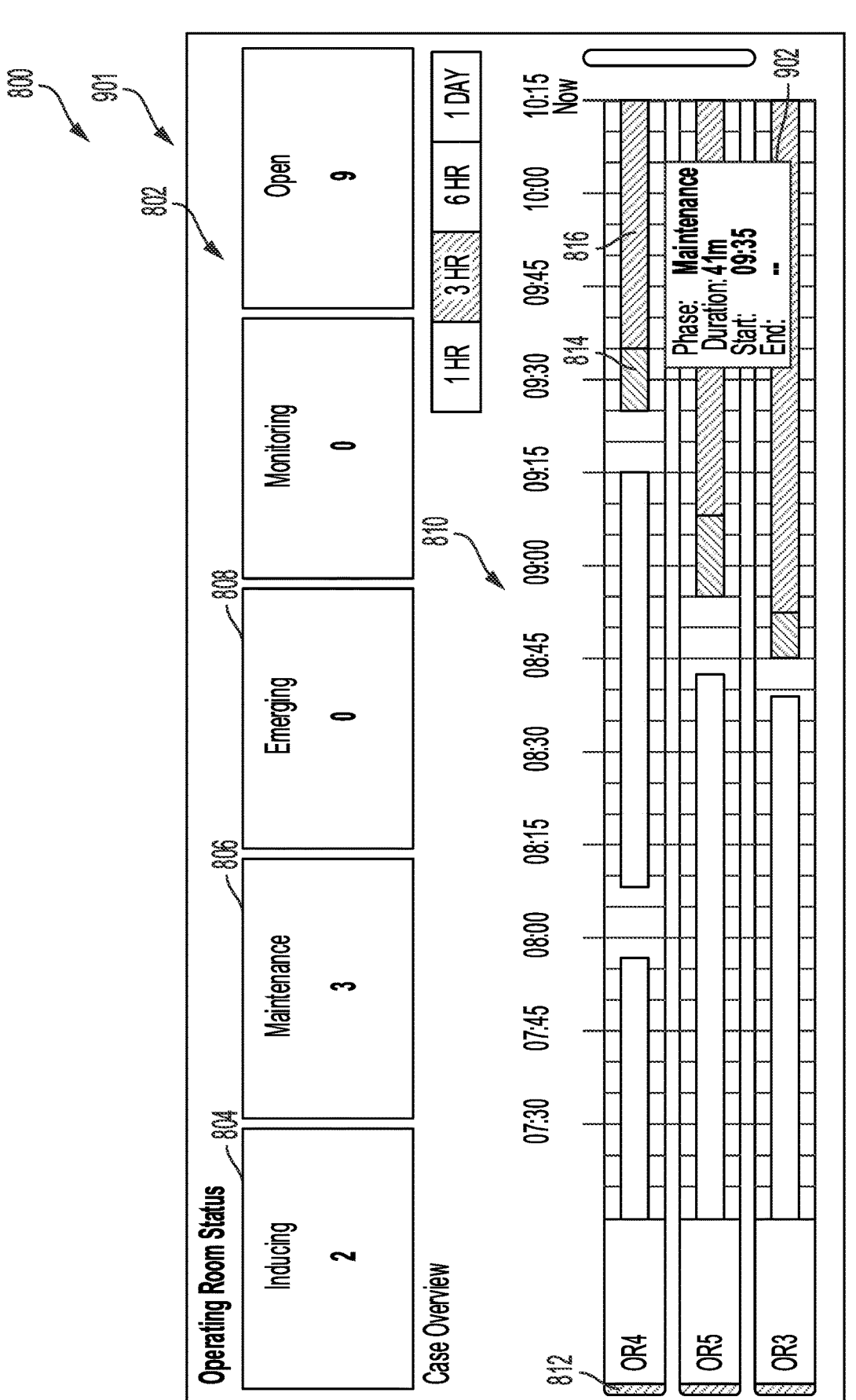
Figure 10:
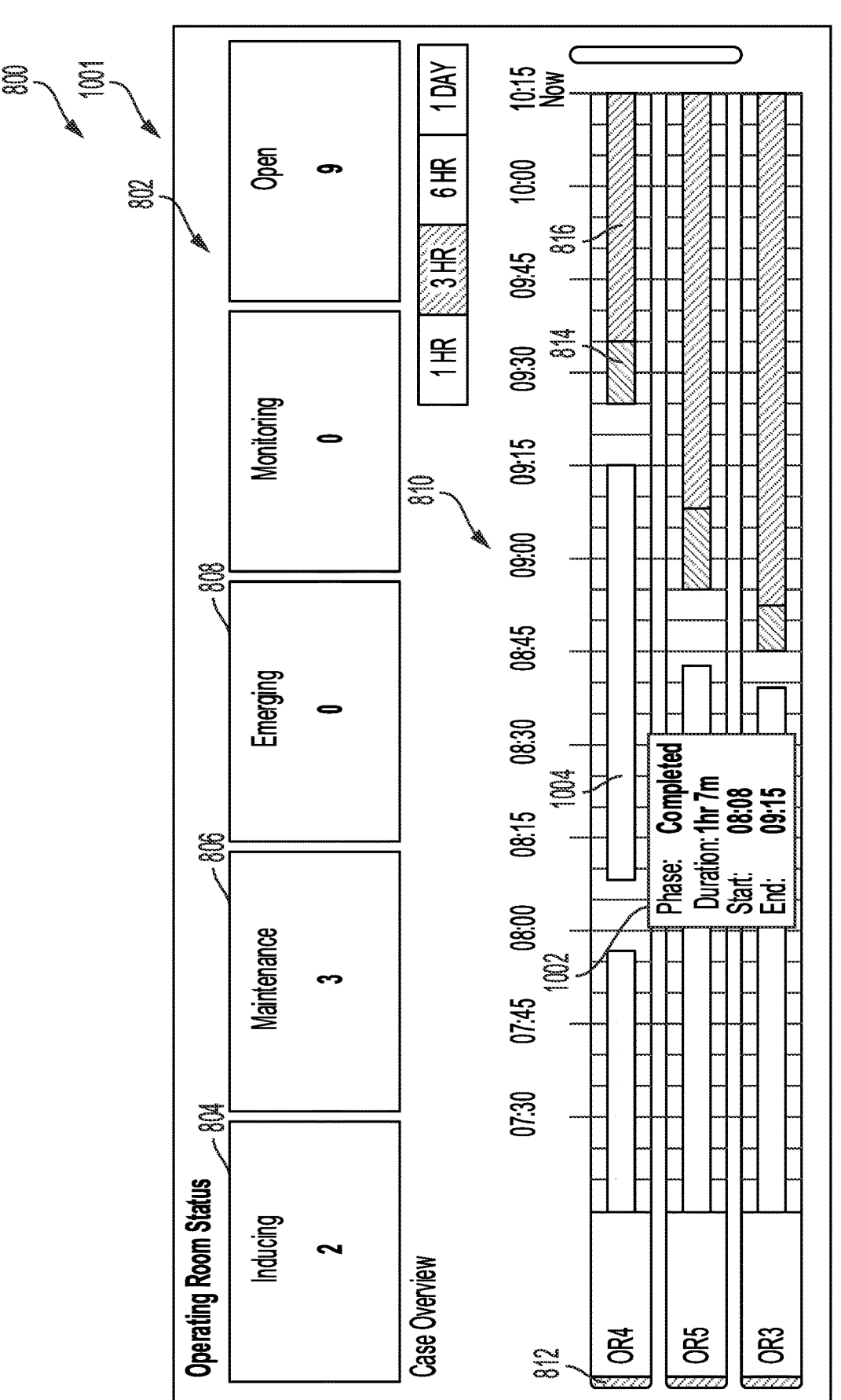

The computing system 120 may distribute medical device data streams to the rules engine 108, and the rules engine 108 may apply the stored event detection rules to the incoming streams of medical device data in order to determine if any phase notifications or results (e.g., indicating a change to a new phase of anesthesia delivery) should be generated. If a phase notification is to be generated, a phase notification may be generated and used to update a GUI to indicate the new phase of anesthesia delivery, with the GUI viewable via the appropriate care provider device(s). Example methods for applying the event detection rules to detect an event and update a GUI are presented below with respect to FIGS. 5-7B, and an example GUI that may be displayed to illustrate anesthesia phase for a plurality of patients is shown in FIGS. 8-10.

The computing system 120 can be implemented in a variety of hardware and/or software implementations and it should be noted that such implementations are not considered to be limiting. For example, it is contemplated that any or all of the computing system 120 may be embodied exclusively in hardware, exclusively in software, exclusively in firmware, or in any combination of hardware, software, and/or firmware. The examples provided herein are not the only way to implement such methods and systems.

In exemplary and non-limiting embodiments of the computing system 120, the computing system 120 is implemented by one or more processors or computing devices. Memory and processors as referred to herein can be stand-alone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to, RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

Figure 3:
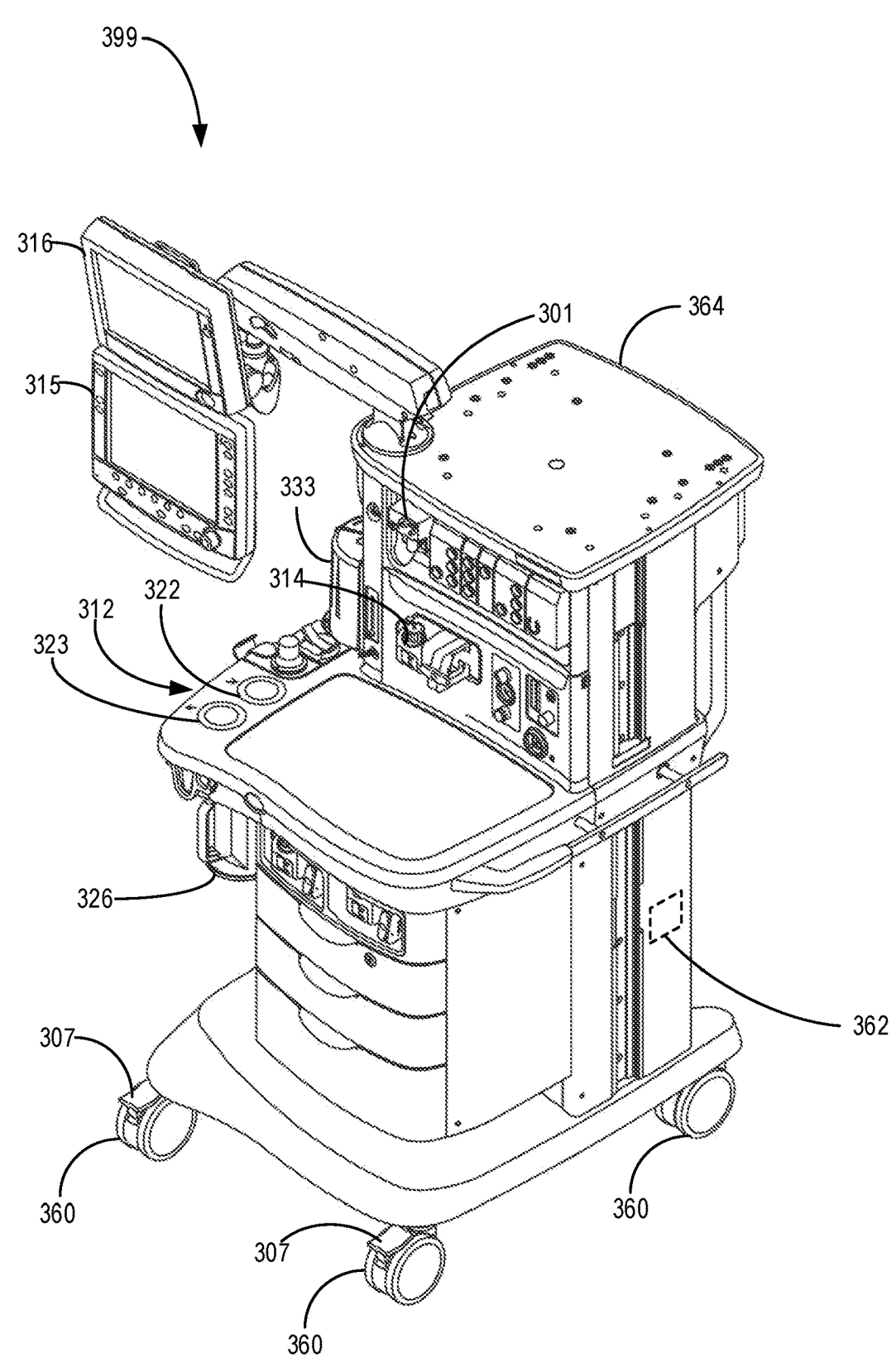
FIG. 3 shows an example anesthesia delivery machine.

FIG. 3 shows an example anesthesia machine 399, which is a non-limiting example of a patient therapy device 16b of FIG. 1. Anesthesia machine 399 includes a frame 364 supported by casters 360, where the movement of the casters may be controlled (e.g., stopped) by one or more locks 307. In some examples, the frame 364 may be formed of a plastic material (e.g., polypropylene). In other examples, the frame 3 64 may be formed from a different type of material (e.g., metal, such as steel).

Anesthesia machine 399 also includes respiratory gas module 301, ventilator 312 (explained in more detail below), vaporizer 314 (explained in more detail below), anesthesia display device 315, and patient monitoring display device 316.

Vaporizer 314 may be in the form of one or more removable cassettes such that a supply of anesthetic agent can be removed from the cassette and such that different types of anesthetic agents can be supplied to the anesthesia machine by simply removing the cassette and replacing it with a different cassette for a different anesthetic agent. When more than one anesthetic agent is to be delivered, more than one cassette may be included with a different anesthetic agent in each cassette. The vaporizer 314 includes a housing having a drug reservoir that contains a supply of anesthetic agent to be delivered to a patient. The drug reservoir may have a discharge opening formed in a back wall of the housing that is configured to receive a discharge tube (not shown), which is part of the anesthesia machine, forming a gas-tight seal for delivery of anesthetic vapor to a patient.

Vaporizer 314 may include at least one absorbent wick within the reservoir. A passageway allows fresh gas from a gas source to pass to the absorbent wick(s). Vaporized liquid from the absorbent wick(s) and accompanying fresh gas may flow to the back of the drug reservoir and out the discharge opening in the housing. A lower portion of the drug reservoir may contain the liquid anesthetic agent and an upper portion of the reservoir may contain the vaporized anesthetic agent and breathing gases. During operation, a combination of temperature and pressure affect the liquid anesthetic agent and cause it to vaporize into the breathing gases. The gases carrying the vaporized agent are then discharged through the discharge opening.

A rear of the anesthesia machine 399 may include one or more pipeline connections to facilitate coupling of the anesthesia machine to pipeline gas sources. Additionally, the rear of the anesthesia machine may include a cylinder yoke, via which one or more gas-holding cylinders may be coupled to the anesthesia machine. Thus, through the pipeline connection and/or cylinder connections, gas may be provided to the anesthesia machine, where the gas may include but is not limited to fresh gas, oxygen, and nitrous oxide. The gas that enters the anesthesia machine may mix with the vaporized anesthetic agent at the vaporizer, as described above, and be supplied to a patient via the ventilator. In some embodiments, the rear of the anesthesia machine may also include a serial port, a collection bottle connection, cylinder wrench storage, anesthesia gas scavenging system, main power inlet, system circuit breaker, equipotential stud, outlet circuit breaker, and isolated electrical outlet.

The ventilator 312 may include an expiratory check valve 322, inspiratory check valve 323, absorber canister 326, and bellows assembly 333. When a patient breathing circuit is coupled to the ventilator, the breathing gases (e.g., fresh gas, oxygen, and/or nitrous oxide mixed with vaporized anesthetic agent) exit the machine from an inspiratory port (which may be positioned at the same location as the inspiratory check valve 323) and travel to a patient. Expiratory gases from the patient re-enter the anesthesia machine via an expiratory port (which may be positioned at the same location as the expiratory check valve 322), where the carbon dioxide may be removed from the expiratory gases via the absorber canister 326.

During operation of the vaporizer 314, an operator (e.g., an anesthesiologist) may adjust an amount of vaporized anesthetic agent that is supplied to a patient by adjusting a flow rate of gases from the gas source(s) (e.g., the gas pipelines) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of the anesthesia machine 399. In one example, a first flow control valve may be positioned between the gas source(s) and the vaporizer 314 and may be actuatable via the flow adjustment devices to a fully opened position, a fully closed position, and a plurality of positions between the fully opened position and the fully closed position.

The anesthesia machine may additionally include one or more bypass valves configured to bypass gases from the gas source(s) around the vaporizer 314. The bypass valves may enable a first portion of gases flowing from the gas source to flow directly from the gas source to the inspiratory port, and a second portion of gases flowing from the gas source may flow through the vaporizer 314 to mix with the vaporized anesthetic agents prior to flowing to the inspiratory port. By adjusting a ratio of an amount of gases flowing to the port via the bypass valves relative to an amount of gases flowing to the port via the vaporizer 314, the operator may control a concentration of vaporized anesthetic agent in gases at the port.

Further, the adjustments described above may be facilitated at least in part based on output from the respiratory gas module 301. Respiratory gas module 301 may be configured to measure various parameters of the gases exiting the vaporizer and/or being provided to the patient. For example, respiratory gas module 301 may measure the concentrations of carbon dioxide, nitrous oxide, and anesthesia provided to the patient. Further, respiratory gas module 301 may measure respiration rate, minimum alveolar concentration, patient oxygen, and/or other parameters. The output from the respiratory gas module 301 may be displayed via a graphical user interface displayed on a display device (e.g., device 315 and/or 316) and/or used by the controller to provide closed-loop feedback control of the amount of anesthesia provided to the patient.

Ventilator 312 may optionally be coupled to a breathing circuit (not shown) including a plurality of tubes (e.g., gas passages). The breathing circuit may be coupled between an airway of a patient (e.g., via a breathing mask positioned to enclose the mouth and/or nose of the patient) and the inspiratory port. Gases (e.g., oxygen, or a mixture of oxygen and vaporized anesthetic agents from vaporizer 314) may flow from the port, through the breathing circuit, and into the airway of the patient, where the gases are absorbed by the lungs of the patient. By adjusting the concentration of vaporized anesthetic agent in the gases as described above, the operator may adjust an amount by which the patient is anesthetized.

During conditions in which the breathing circuit is coupled to the airway, anesthetic agent and/or fresh gases may flow into the airway (e.g., be inhaled by the patient) via the inspiratory check valve 323. For example, inspiratory check valve 323 may open automatically (e.g., without input or adjustment by the operator) in response to inhalation of the patient, and may close automatically in response to exhalation of the patient. Similarly, the expiratory check valve 322 may open automatically in response to exhalation of the patient, and may close automatically in response to inhalation of the patient.

In some examples, the operator may alternately and/or additionally control one or more operating parameters of the anesthesia machine 399 via an electronic controller 362 of the anesthesia machine 399 (shown schematically by FIG. 3). Controller 362 includes a processor operatively connected to a memory. The memory may be a non-transitory computer-readable medium and may be configured to store computer executable code (e.g., instructions) to be processed by the processor in order to execute one or more routines. The memory may also be configured to store data received by the processor. Controller 362 may be communicatively (e.g., wired or wirelessly) coupled to one or more external or remote computing devices, such as computing system 120, and may be configured to send and receive various information, such as measured patient monitoring parameters (e.g., the output from the respiratory gas module 301), electronic medical record information, procedure information, and so forth.

The controller receives signals from the various sensors of the anesthesia machine 399 and employs the various actuators of the anesthesia machine 399 to adjust operation of the anesthesia machine 399 based on the received signals and instructions stored on the memory of the controller. For example, the flow of gases to the inspiratory port may be controlled via an input device (e.g., keyboard, touchscreen, etc.) coupled to the electronic controller of the anesthesia machine 399. The controller may be electrically coupled to display device 315 and/or 316 in order to display operating parameters of the anesthesia machine 399. The controller may receive signals (e.g., electrical signals) via the input device and may adjust operating parameters of the anesthesia machine 399 in response (e.g., responsive) to the received signals. For example, the operator may input a desired flow rate of gases (e.g., oxygen) flowing from the gas source to the patient and/or vaporizer 314.

A corresponding valve position of one or more valves of the anesthesia machine (e.g., a position of one or more bypass valves, as described above) may be empirically determined and stored in a predetermined lookup table or function on the controller. For example, the controller may receive the desired flow rate of gases via the input device and may determine an amount of opening of the one or more bypass valves corresponding to the desired flow rate based on the lookup table, with an input being the desired flow rate and an output being the valve position. The controller may transmit an electrical signal to an actuator of the valve in order to adjust the valve position. In some examples, the controller may compare the desired flow rate of gases to a measured flow rate of gases as measured by a flow rate sensor (e.g., an inspiratory flow sensor).

Controller 362 is shown in FIG. 3 for illustrative purposes, and it is to be understood that controller 362 may be located internally of anesthesia machine 399 and thus may not be visible externally on anesthesia machine. Controller 362 may include multiple devices/modules that may be distributed across anesthesia machine 399.

Figure 4:
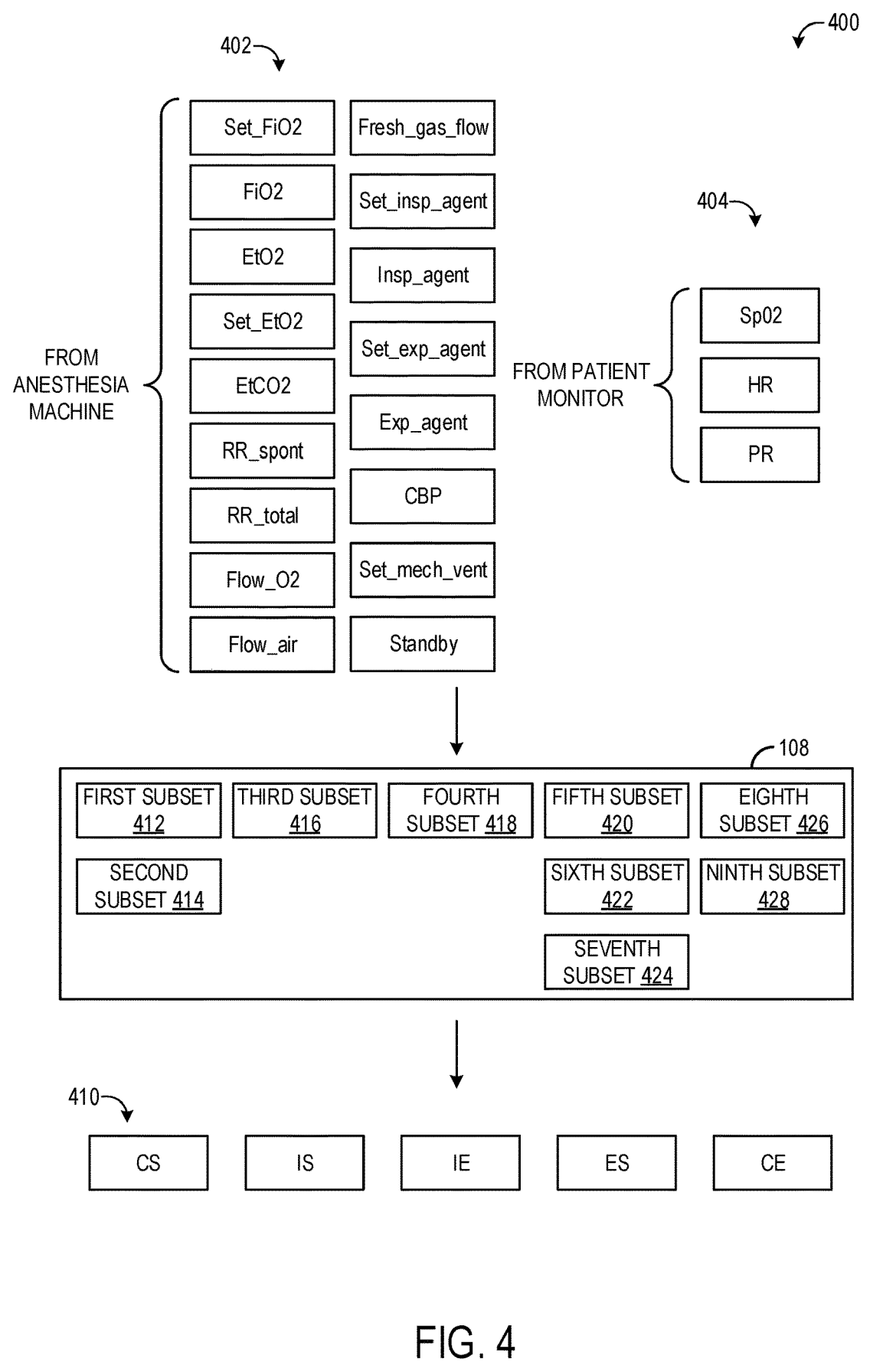

FIG. 4 schematically shows example monitoring parameters 400 (e.g., medical device data) that may be processed via the computing system 120 using phase detection rules of rules engine 108 in order to determine whether an event signaling a change to a new phase of anesthesia delivery has occurred. The parameters 400 may be non-limiting examples of the medical device data discussed above with respect to FIGS. 1-3. The parameters 400 may include a first set of parameters 402 that are obtained from an anesthesia delivery machine (e.g., anesthesia machine 399), which may include one or more of measured fraction of inspired oxygen (FiO2); measured end-tidal oxygen (EtO2); measured end-tidal CO2 (EtCO2); set FiO2 (Set_FiO2); set EtO2 (Set_EtO2); spontaneous respiration rate (RR_spont); total respiration rate (RR_total); set mechanical ventilation (Set_mech_vent); set inspired anesthetic agent (Set_insp_agent); set expired anesthetic agent (Set_exp_agent); measured inspired anesthetic agent (Insp_agent); measured expired anesthetic agent (Exp_agent); fresh gas flow rate (Fresh_gas_flow); O2 flow rate (Flow_O2); air flow rate (Flow_air); cardiac bypass mode (CBP); and anesthesia machine standby state (standby). It should be appreciated that different anesthesia delivery machines may output different monitoring parameters. For example, some anesthesia delivery machines may not output the set FiO2 (Set_FiO2), the set EtO2 (Set_EtO2), and/or the set inspired anesthetic agent (Set_insp_agent) or the set expired anesthetic agent (Set_exp_agent). As a specific example, a premium or new-generation anesthesia delivery machine having a first configuration may output all the parameters listed above, while a first prior-generation anesthesia delivery machine having a second configuration may output all the parameters listed above other than the set inspired anesthetic agent (Set_insp_agent) and the set expired anesthetic agent (Set_exp_agent). A second prior-generation anesthesia delivery machine having a third configuration may output all the parameters listed above other than the set FiO2 (Set_FiO2), the set EtO2 (Set_EtO2), the set inspired anesthetic agent (Set_insp_agent), and the set expired anesthetic agent (Set_exp_agent).

The parameters 400 may optionally include a second set of parameters 404 that are obtained from one or more patient monitoring devices not included as part of the anesthesia machine, including one or more of oxygen saturation measurement (SpO2), heart rate (HR), and pulse rate (PR).

The rules engine 108 may select a set of rules based on the parameters 400 (e.g., based on whether or not the second set of parameters 404 are available) and apply the selected set of rules to determine if an event of a plurality of events 410 is detected, wherein the event signals a change to a new phase of anesthesia delivery. The plurality of events 410 may include case start (CS), start of induction (induction starts, IS), end of induction (induction end, IE), start of emergence (emergence start, ES), and case end (CE). In some examples, the plurality of events may also include end of emergence (EE), which may occur before the case officially ends. Specifically, each event may have one or more subsets of rules that can be applied to detect that event and an appropriate subset may be selected based on the available monitoring parameters.

As shown, the rules engine 108 includes nine subsets of rules. A first subset 412 and a second subset 414 of rules may each be applied to detect case start. The first subset 412 may be applied when the received monitoring parameters includes at least one parameter from the second set of monitoring parameters 404, and the second subset 414 may be applied with the received monitoring parameters do not include at least one parameter from the second set of monitoring parameters 404. A third subset 416 of rules may be applied to detect induction start. A fourth subset 418 of rules may be applied to detect induction end. A fifth subset 420, a sixth subset 422, and a seventh subset 424 of rules may each be applied to detect emergence start. The fifth subset 420 may be applied when each of the first set of parameters 402 is received (and specifically when Set_FiO2 and/or Set_EtO2 is received and when Set_insp_agent and/or Set_exp_agent is received). The sixth subset 422 may be applied when Set_FiO2, Set_EtO2, Set_insp_agent, and Set_exp_agent are not received. The seventh subset 424 may be applied when Set_FiO2 and/or Set_EtO2 is received but Set_insp_agent and Set_exp_agent are not received. An eighth subset 426 and a ninth subset 428 of rules may each be applied to detect case end. The eighth subset 426 may be applied when the received monitoring parameters include at least one parameter from the second set of monitoring parameters 404 and the ninth subset 428 may be applied with the received monitoring parameters do not include at least one parameter from the second set of monitoring parameters 404.

Thus, a set of rules may be assembled by selecting various subsets of rules based on the received monitoring parameters. As a first example, if the anesthesia delivery machine has the first configuration and parameters from the monitoring device are received in addition to the parameters from the anesthesia delivery machine, a first set of rules may be assembled that includes the first subset 412, the third subset 416, the fourth subset 418, the fifth subset 420, and the eighth subset 426. As a second example, if the anesthesia delivery machine has the first configuration and parameters from a monitoring device are not received in addition to the parameters from the anesthesia delivery machine, a second set of rules may be assembled that includes the second subset 414, the third subset 416, the fourth subset 418, the fifth subset 420, and the ninth subset 428. As a third example, if the anesthesia delivery machine has the second configuration and parameters from the monitoring device are received in addition to the parameters from the anesthesia delivery machine, a third set of rules may be assembled that includes the first subset 412, the third subset 416, the fourth subset 418, the sixth subset 422, and the eighth subset 426. As a fourth example, if the anesthesia delivery machine has the second configuration and parameters from the monitoring device are not received in addition to the parameters from the anesthesia delivery machine, a fourth set of rules may be assembled that includes the second subset 414, the third subset 416, the fourth subset 418, the sixth subset 422, and the ninth subset 428. As a fifth example, if the anesthesia delivery machine has the third configuration and parameters from the monitoring device are received in addition to the parameters from the anesthesia delivery machine, a fifth set of rules may be assembled that includes the first subset 412, the third subset 416, the fourth subset 418, the seventh subset 424, and the eighth subset 426. As a sixth example, if the anesthesia delivery machine has the third configuration and parameters from the monitoring device are not received in addition to the parameters from the anesthesia delivery machine, a sixth set of rules may be assembled that includes the second subset 414, the third subset 416, the fourth subset 418, the seventh subset 424, and the ninth subset 428.

In addition to accounting for different anesthesia delivery machine configurations and the presence or absence of parameters from patient monitors, the rules stored within the rules engine 108 and applicable to detect the events described herein may also account for certain use cases that may otherwise trigger false event detections or missed event detections. For example, when an anesthesia delivery machine is employed during a cardiac bypass procedure, the start of emergence may be missed (and a false indication of induction end/maintenance start may be provided) if the rules were to rely on mechanical ventilation status alone, as termination of mechanical ventilation is a signature of the start of emergence for all patients other than those undergoing cardiac bypass. Accordingly, the subsets of rules applied to detect emergence start (e.g., the fifth, sixth, and seventh subsets described above) may account for cardiac bypass by requiring, if the cardiac bypass mode is on or in passive mode, that parameters other than mechanical ventilation status be used to indicate emergence start, such as two or more of an increase in the set value of FiO2 or estimated set FiO2, a decrease (to 0) of set or inspired anesthetic agent, and an increase in fresh gas flow rate. As another example, detected changes to anesthetic agent concentration (whether set concentration, inspired concentration, or expired concentration) may be used to detect emergence start and case end. However, some patients may not receive anesthetic agent via the patient breathing circuit as described above with respect to FIG. 3, but may instead receive anesthetic agent intravenously (referred to as total intravenous anesthetic agent delivery, or TIVA). In such cases, anesthetic agent concentration is not detectable by the anesthesia delivery machine. Accordingly, when the received patient monitoring parameters do not include anesthetic agent concentration (or when the anesthetic agent concentration is invalid or blank), alternate rules may be applied to detect start of emergence and case end. Further still, the rules that rely on anesthetic agent concentration may also account for multiple different anesthetic agents by relying on a weighted sum of the various anesthetic agent concentrations.

In this way, a first set of rules may be applied when the received patient monitoring parameters include an expected set of monitoring parameters, e.g., the best possible monitoring parameters available that allow for the most rapid and accurate detection of certain events (e.g., case start, emergence start, case end). As a specific example, relying on the parameters from the patient monitor (e.g., SpO2, HR, or PR) to detect case start may allow for an earlier detection of case start than relying on parameters from the anesthesia delivery machine (e.g., FiO2 and EtO2). As another example, the expected set of monitoring parameters may include set FiO2, set EtO2, and/or set anesthetic agent concentration, which may be used to detect emergence start (particularly during cardiac bypass) more accurately than relying on estimated FiO2 and/or inspired anesthetic agent. However, when the expected set of monitoring parameters are not available, alternative rules may be applied that still allow for detection of the events, even if slightly delayed or with lower accuracy.

Thus, the method for phase detection disclosed herein uses anesthesia machine parameters to detect events signaling a change in anesthesia phases as well as CS and CE events. In contrast, existing solutions only assess brain activity dependent states or depend on explicit clinician inputs. Accordingly, the method disclosed herein does not require additional patient devices (e.g., EEG devices), and thus may be less expensive, more comfortable for patients, and/or more accurate and faster than existing solutions, as well as allowing for detection of all events including case start and case end. Moreover, the proposed method is a real-time and state-less multi-parametric approach which would work for all types of anesthesia machines, special cases such as cardiac bypass, total intravenous cases (TIVA cases), and with or without monitor data availability. By being state-less, the proposed method does not rely on a previously-determined anesthesia phase but instead identifies whether or not an event is detected at each observation window (e.g., sliding window of received parameters), without knowing the current or previous anesthesia phase or previously-identified event. In doing so, the proposed method may demand less memory and may not be unduly influenced by prior false event detections, thereby increasing processing efficiency and system performance.

Figure 5:
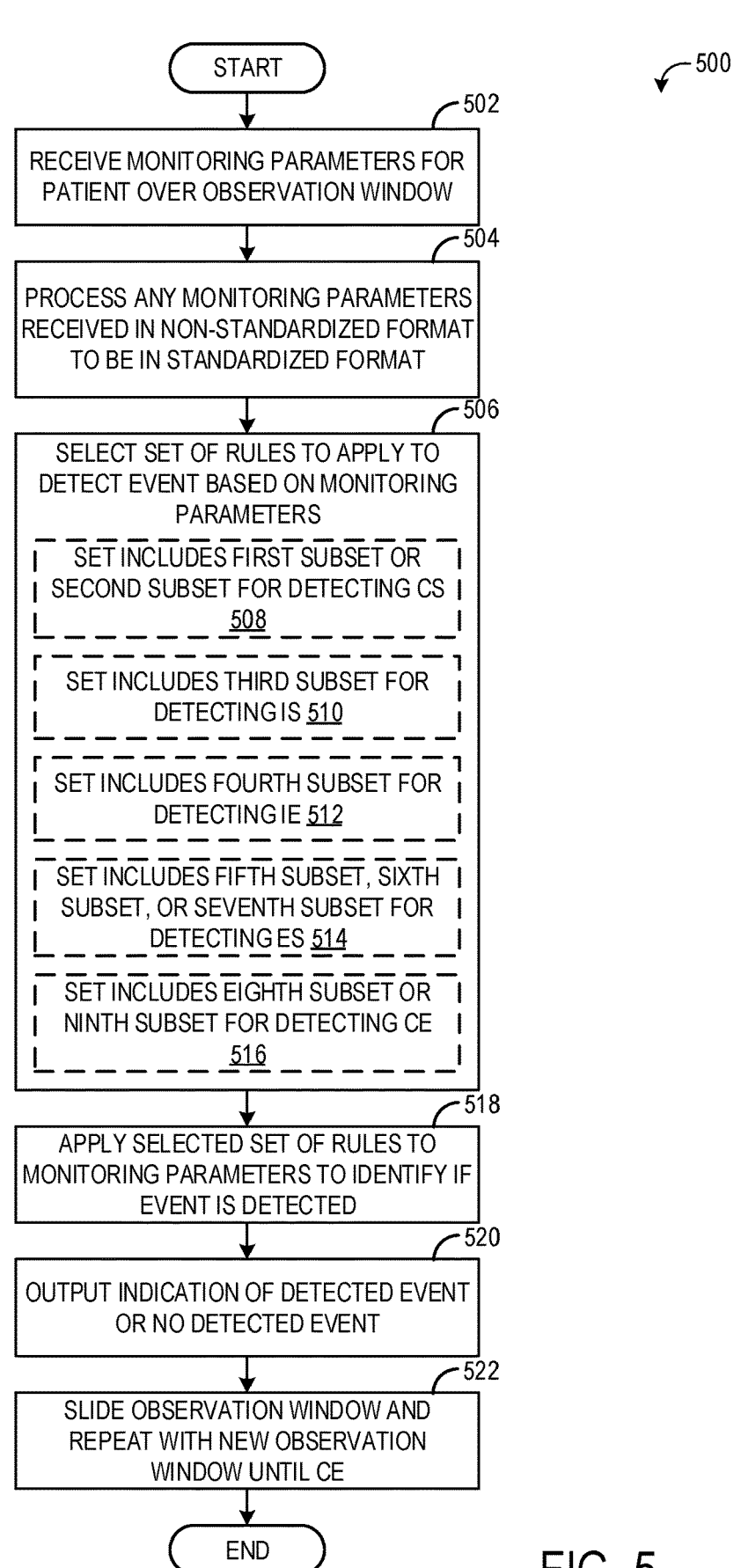
FIG. 5 is a flow chart showing an example method for automatically detecting an event signaling a change in anesthesia phase.

FIG. 5 shows a high-level method 500 for detecting anesthesia delivery events for a patient. Method 500 may be implemented with the system 10 of FIGS. 1 and 2. Method 500 may be carried out according to instructions stored in non-transitory memory and executed by one or more processors, such as memory and processor(s) of computing system 120 of FIG. 2.

At 502, method 500 receives monitoring parameters for a patient over an observation window. The monitoring parameters may be received from an anesthesia delivery machine, such as anesthesia machine 399 of FIG. 3. In some examples, the monitoring parameters may also be received from a patient monitor, such as one of the physiological monitoring devices 16a of FIG. 1. The monitoring parameters may include some or all of the monitoring parameters 400 described above with respect to FIG. 4. Further, as explained above with respect to FIGS. 1 and 2, the monitoring parameters may be ingested by the computing system and stored (at least temporarily). The observation window may include a set period of time over which the monitoring parameters are received and stored for further processing to detect an event, as will be explained below. The observation window may thus include a suitable duration of time, such as one minute. The observation window may be selected to allow sufficient time to detect changes in selected monitoring parameters that are indicative of an event signaling a new phase of anesthesia delivery, yet short enough to minimize the overall amount of data stored and allow for rapid event detection (e.g., avoid undue delays in detecting a shift to a new phase).

At 504, may method 500 includes processing any monitoring parameters received in a non-standardized format to be converted into a standardized format. The processing into the standardized format may be performed in order to prepare the received monitoring parameter data for evaluation via a selected set of rules of the rules engine to detect an event, as explained in more detail below, and thus the standardized format may include a format usable by the rules engine. The processing may include interpolating one or more monitoring parameters to include a standardized number of data points. For example, some monitoring parameters may be recorded and/or sent at a relatively low frequency (e.g., once every 10 seconds) compared to other monitoring parameters that may be recorded and/or sent at a relatively high frequency, such as once per second. Thus, the monitoring parameters recorded and/or sent at the lower frequency(ies) may be interpolated to increase the number of data points for those monitoring parameters over the observation window. In this way, any missing values in the raw data from the anesthesia machine and optionally patient monitor may be replaced by forward filling the raw data in the observation window with a prior segment of data (e.g., the prior 30 seconds' worth of data) to maintain data validity and assist parameter comparison. Other examples of processing may include averaging, filtering, determination of trends (e.g., change in a monitoring parameter over the observation window), etc. Still other processing may be applied, such as conversion to a standardized communication protocol. For example, some anesthesia machines may communicate according to a first protocol while other anesthesia machines may communicate according to a second protocol, and the processing may include converting monitoring parameters received in accordance with the second protocol to the first protocol.

At 506, method 500 includes selecting a set of rules to apply to detect if an event has occurred, based on the received monitoring parameters. The set of rules may be selected from among a plurality of subsets of rules based on the received monitoring parameters. As indicated at 508, the selected set of rules may include a first subset or a second subset of rules for detecting case start. The first subset may be selected when the received monitoring parameters includes one or more parameters received from a patient monitor (e.g., heart rate, SpO2, pulse rate) while the second subset may be selected when the received monitoring parameters do not include one or more parameters received from a patient monitor. As indicated at 510, the selected set of rules may include a third subset of rules for detecting induction start and a fourth subset of rules for detecting induction end, as indicated at 512. The selected set of rules may include a fifth subset, a sixth subset, or a seventh subset of rules for detecting emergence start, as indicated at 514. One of the fifth, sixth, and seventh subsets of rules may be selected based on the configuration of the anesthesia delivery machine, which may be determined from the received monitoring parameters. The fifth subset may be selected when the received monitoring parameters include set FiO2 and/or set EtO2 and set inspired anesthetic agent and/or set expired anesthetic agent. The sixth subset may be selected when none of the set FiO2, the set EtO2, the set inspired anesthetic agent, and the set expired anesthetic agent is received. The seventh subset may be selected when the set FiO2 and/or the set EtO2 is received but the set inspired anesthetic agent and the set expired anesthetic agent are not received. As indicated at 516, the selected set of rules may include an eighth subset or a ninth subset of rules for detecting case end. The eighth subset may be selected when the received monitoring parameters includes one or more parameters received from a patient monitor (e.g., heart rate, SpO2, pulse rate) while the ninth subset may be selected when the received monitoring parameters do not include one or more parameters received from a patient monitor.

At 518, the selected set of rules is applied to the received monitoring parameters to identify if an event is detected. Additional details about applying the selected set of rules to the monitoring parameters to identify if an event is detected are provided below with respect to FIGS. 7A and 7B. As explained previously, the events that may be detected include events that signal a change to a new phase of anesthesia delivery, and as such may be somewhat transient events. Accordingly, for each observation window, an output may be generated that indicates that an event was detected (and if so, which event) or that no event was detected, as indicated at 520, depending on the result of the set of rules applied to the monitoring parameters. When no event is detected, the new phase of anesthesia delivery has not happened yet and the current phase of anesthesia delivery may be ongoing. However, the method for identifying if an event has occurred as described herein with respect to FIG. 5 may be stateless, in that a prior or current anesthesia phase is not known. Accordingly, when an event is not detected, the indication that is output may not include the current anesthesia phase.

At 522, method 500 includes sliding the observation window and repeating the method (e.g., receiving the monitoring parameters for the patient over the new observation window, processing the monitoring parameters, selecting the set of rules, applying the selected set of rules, and outputting the indication), which may be repeated until case end is detected. The observation window may be slid by a suitable amount, such as one second. In this way, the indication of whether or not an event was detected may be repeated over the course of the anesthesia delivery for the patient with newly-obtained monitoring parameters at a desired frequency (e.g., each second), using the past one minute (or other suitable duration) of received monitoring parameters. It is to be appreciated that method 500 may be performed for each patient/operating room undergoing or about to undergo anesthesia delivery at a given medical facility, unit, or ward.

Figure 6:
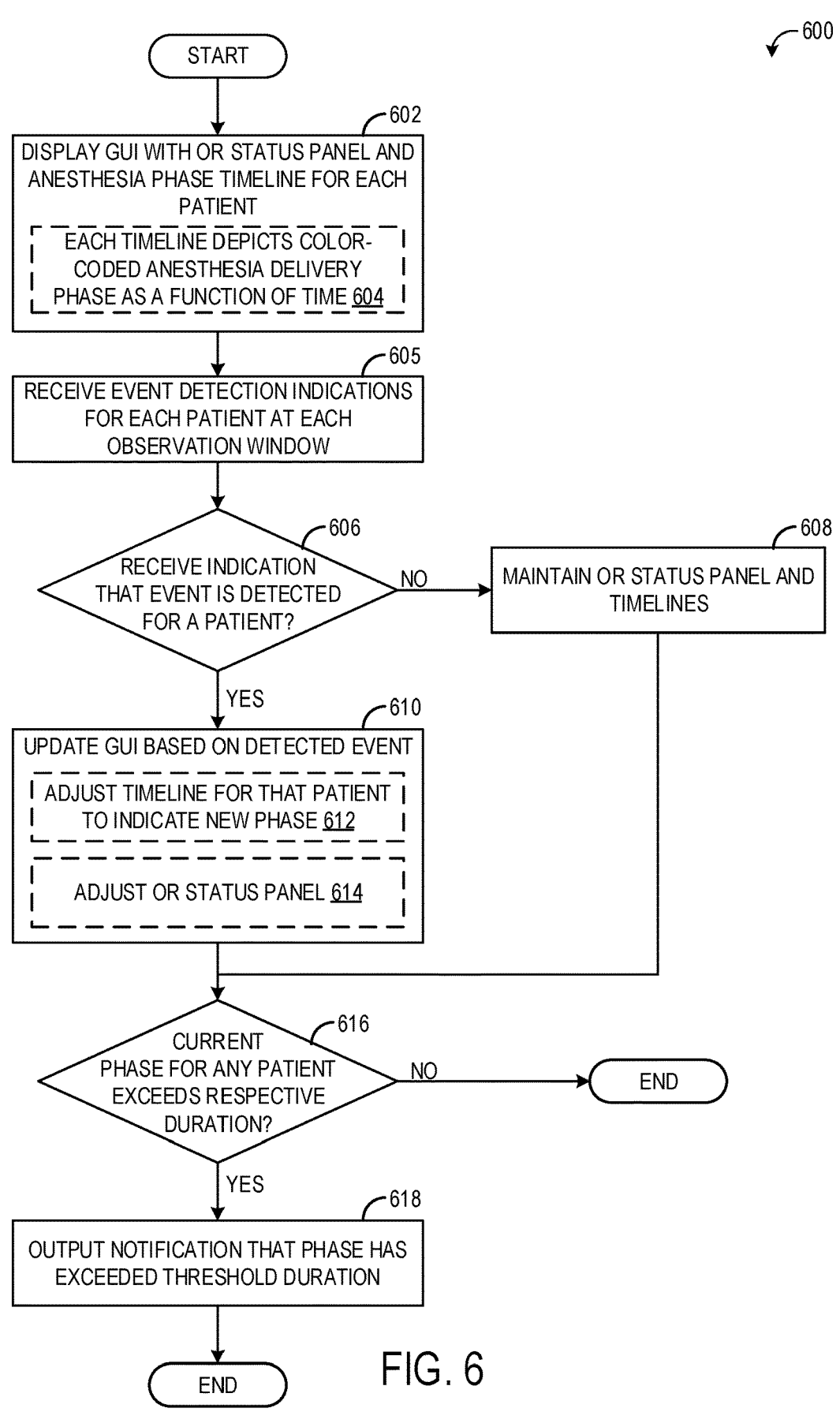
FIG. 6 is a flow chart showing an example method for updating a graphical user interface based on an event detected according to the method of FIG. 5.

FIG. 6 is a method 600 for displaying a current anesthesia phase for each of a plurality of patients. Method 600 may be implemented with the system 10 of FIGS. 1 and 2. Method 600 may be carried out according to instructions stored in non-transitory memory and executed by one or more processors, such as memory and processor(s) of computing system 120 of FIG. 2. In some examples, method 600 may instead be carried out according to instructions stored in non-transitory memory and executed by one or more processors of a computing system in communication with computing system 120 of FIG. 2, such as a care provider device (e.g., first care provider device 134).

At 602, a graphical user interface (GUI) is displayed (e.g., on a display device included as part of communicatively coupled to the computing system) that includes an operating room (OR) status panel and anesthesia phase timeline for each of a plurality of patients. The plurality of patients may be undergoing, or about to undergo, anesthesia delivery as part of a surgical or other medical procedure at a specific medical facility being tracked by the computing system. For example, each patient of the plurality of patients may be located in a respective operating room of the medical facility. The OR status panel may include a summary of current anesthesia delivery phase for the plurality of patients, such as the number of patients in induction, the number of patients in maintenance, and the number of patients in emergence. The OR status panel may further include a number of operating rooms that are open (e.g., do not currently have a patient accommodated therein). Each anesthesia phase timeline depicts color-coded anesthesia phases as a function of time, as indicated at 604. For example, a first anesthesia phase timeline for a first patient may begin at case start, which may be indicated on the timeline in a first color, and transition to induction 10 minutes after case start, wherein induction may be indicated on the timeline in a second color. Example GUIs including OR status panels and timelines for a plurality of patients are shown in FIGS. 8-10.

At 605, method 600 includes receiving an event detection indication for each patient at each observation window. The indications may be generated according to method 500, for example. As explained above, an event may include one of case start, induction start, induction end, emergence start, and case end. The method to identify if an event has occurred (e.g., method 500) may be executed for each patient that is about to start receiving anesthesia or is currently receiving anesthesia. In some examples, rather than identifying the patients themselves, the method may be performed for each operating room or each anesthesia delivery machine that is in operation as a proxy for identifying a patient. As explained above with respect to FIG. 5, during each observation window, for each patient (or operating room or anesthesia delivery machine), an indication may be generated of whether an event has been detected for that patient or whether an event has not been detected for that patient. The computing system executing method 600 may receive each indication for each observation window for each patient, and each indication may be time-stamped. In some examples, each indication may be stored in a table or other data structure. Alternatively, once an indication indicating case start has been detected for a given patient is received, the table may be updated to indicate the current phase of anesthesia delivery (e.g., case start) and time the current phase started. The current phase may be maintained until an indication is received that induction start for the given patient has been detected, at which point the table may be updated to indicate that the current phase of anesthesia delivery is induction and the time at which induction started for the given patient. In either example, the table may store the current phase of anesthesia delivery for each patient as well as each known prior phase and the timing/duration of each phase.

At 606, method 600 includes determining if an indication that an event has been detected for a patient has been received. From the indications received at 605, the method may determine whether any of the indications indicate that an event was detected, or determine whether all the indications indicate no event was detected. If an indication that an event for a patient has been detected is not received (e.g., the most-recently received indications all indicate that no event was detected), method 600 proceeds to 608 to maintain the OR status panel and each timeline in the current state, other than advancing time for each timeline. For example, referring back to the first timeline for the first patient discussed above, the first timeline may continue to indicate that the first patient is undergoing induction, as no event indicating otherwise has been detected.

If an indication that an event for a patient has been detected is received, method 600 proceeds to 610 to update the GUI based on the detected event. Updating the GUI may include adjusting the timeline for that patient to indicate the transition to the new phase, as indicated at 612. The adjustment to the timeline may include initiating the timeline (when the event that is detected is case start), adjusting the phase indicated by the timeline (when the event that is detected is induction start, induction end, or emergence start), or terminating the timeline (when the event that is detected is case end). For example, an indication may be received that induction end has been detected for the first patient. In response, the first timeline for the first patient may be updated to indicate the patient has entered maintenance, which is the phase following induction. The current phase (e.g., maintenance) may be visualized on the timeline via a third color, for example. Additionally, updating the GUI based on the detected event may include adjusting the OR status panel, as indicated at 614. When a change to a new phase of anesthesia delivery is detected via detection of an event, the OR status panel may be adjusted to show the new total number of patients in each phase, such as reducing the total number of patients in induction and increasing the total number of patients in maintenance in response to detecting induction end for the first patient.

At 616, method 600 determines if a duration of a current phase of anesthesia delivery for any patient exceeds a respective threshold. As explained above, each anesthesia phase (current and prior) for each patient may be logged/tracked via the table and indicated via the GUI. Each phase may have an expected duration (or range of expected durations) that the phase is to last, and a phase that lasts longer than the expected duration may be indicative of issues that may warrant clinician or administrative attention. For example, case start lasting longer than a first threshold duration (e.g., ten minutes) may indicate a delay in progressing the patient to reception of anesthesia due to unavailability of equipment and/or personnel. An emergence phase that lasts longer than a second threshold duration (e.g., 20 minutes) may indicate that the patient is exhibiting deep anesthesia and/or that logistical issues (e.g., lack of beds or personnel) are hindering movement of the patient out of the operating room. Any of these issues may warrant notification of administrative and/or clinical staff in order to address the issue (e.g., by moving personnel, adjusting scheduling of future procedures, ensuring a supervising anesthesiologist is attending to the patient).

If a duration of a current phase for a given patient exceeds a threshold for that phase, method 600 proceeds to 618 to output a notification (e.g., an alarm, message, etc.) that the phase has exceeded the threshold duration. The notification may be displayed on the GUI, sent to one or more care provider devices, or otherwise output for administrative and/or clinical staff to hear or view. Otherwise, method 600 may end. It is to be appreciated that the detection of whether or not any phases have exceeded a respective threshold may be performed at any time during execution of method 600. Further, method 600 may be repeated as each observation window for each patient slides, such that the GUI may be updated at the same frequency (e.g., once per second) that the event detection indications are generated.

Thus, method 600 provides for updates to a GUI to indicate current anesthesia phase for each of a plurality of patients based on anesthesia event detections generated automatically according to method 500. While method 600 includes updates to the GUI any time an indication is received that indicates an event was detected, in some examples the GUI may be updated only once a threshold number of indications of the same event have been consecutively received (e.g., two, three) or updated only once a last indication of an event is received (e.g., once an indication indicating no event has been detected is received following at least one indication that an event has been detected having been received). In doing so, false positive indications of the change to a new phase of anesthesia delivery may be avoided.

Figure 7A:
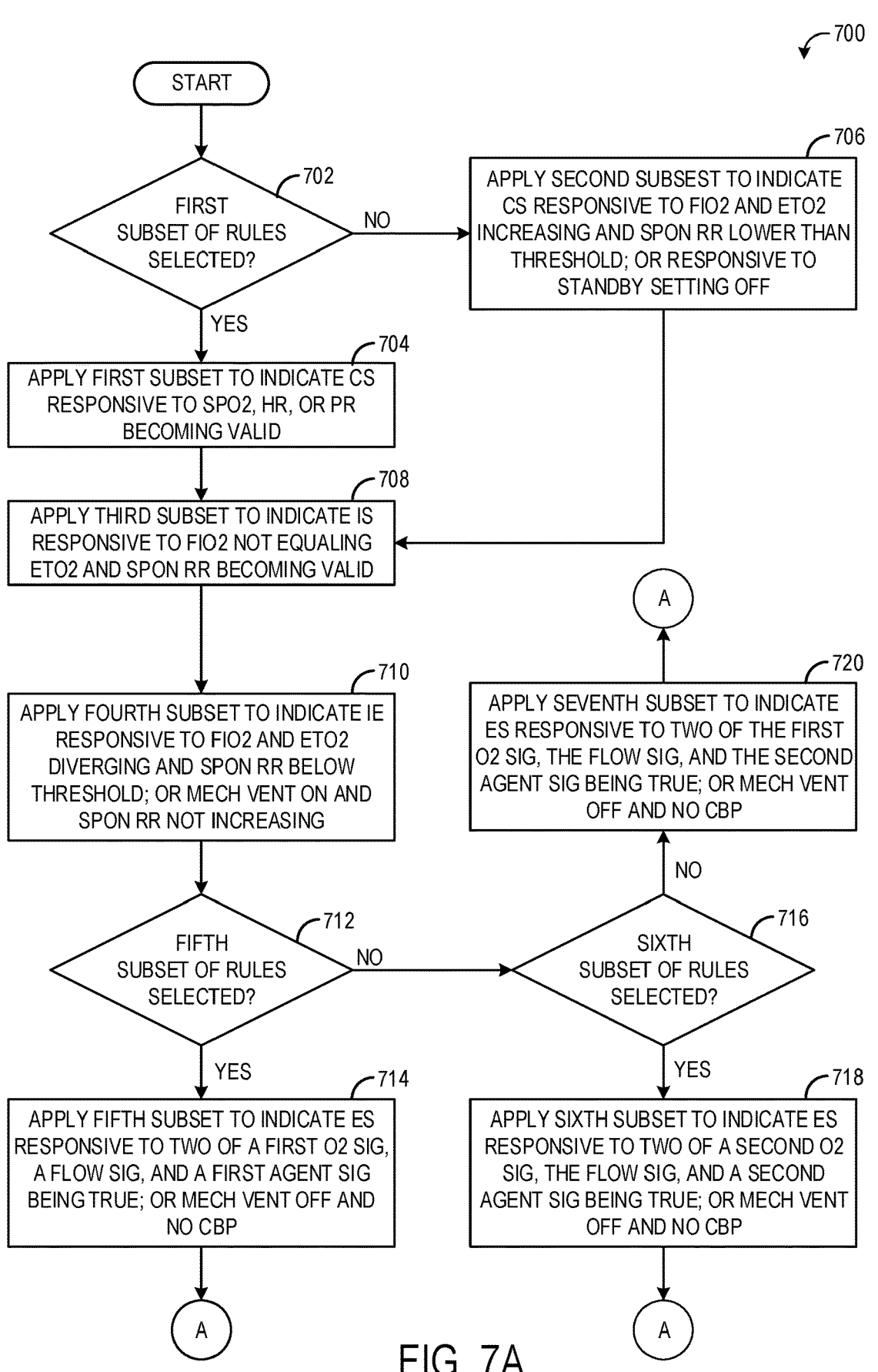
FIGS. 7A and 7B are a flow chart showing an example method for applying a selected set of rules to detect an event signaling a change in anesthesia phase.
Figure 7B:
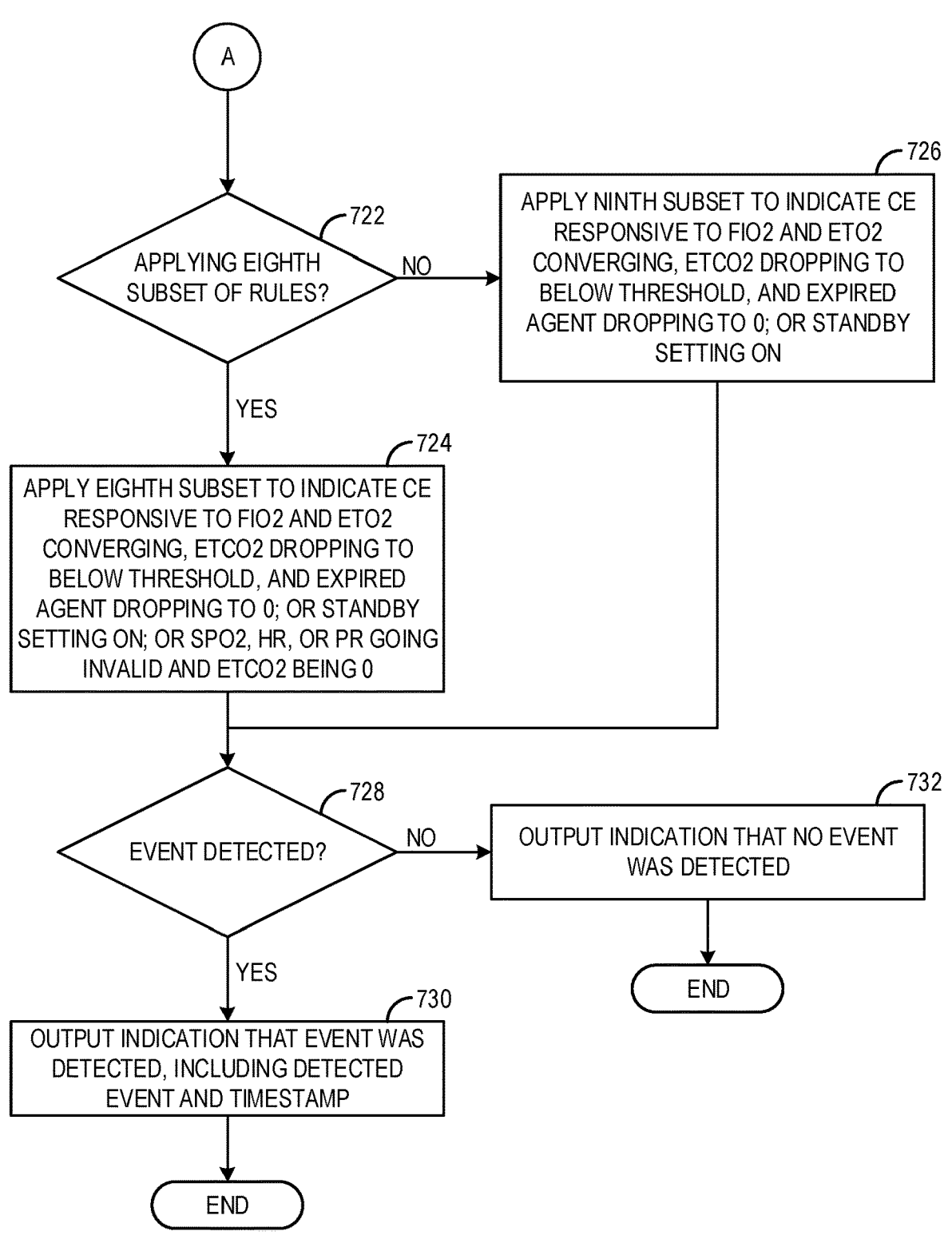

Turning now to FIGS. 7A and 7B, a method 700 is shown for applying a selected set of rules to received monitoring parameters of a patient in order to detect an event signaling a change in anesthesia delivery to the patient. Method 700 may be implemented with the system 10 of FIGS. 1 and 2. Method 700 may be carried out according to instructions stored in non-transitory memory and executed by one or more processors, such as memory and processor(s) of computing system 120 of FIG. 2. In some examples, method 700 may be carried out as part of method 500, e.g., at 518 of method 500.

At 702, method 700 includes determining if the selected set of rules includes a first subset of rules. As described above, the selected set of rules may include either a first subset or a second subset of rules that may be applied to detect case start, depending on whether the received monitoring parameters include any parameters received from a patient monitor. The selected set of rules may include the first subset when parameters are received from the patient monitor. If the selected set of rules includes the first subset, method 700 proceeds to 704 to apply the first subset of rules to the received monitoring parameters over the observation window in order to indicate case start responsive to any one of SpO2, HR, or PR becoming valid (e.g., changing from an invalid number/value such as zero or blank to a valid number/value). Thus, when parameters from the patient monitor are received, case start may be indicated when SpO2, HR, or PR become valid.

If the selected set of rules does not include the first subset, method 700 proceeds to 706 to apply the second subset of rules to indicate case start responsive to measured FiO2 and EtO2 increasing and spontaneous respiration rate being lower than a threshold respiration rate (such as 0.1, or if the spontaneous respiration rate output is blank); or alternatively, responsive to the anesthesia delivery machine standby setting being switched off/out of standby. Thus, when parameters from the patient monitor are not received, case start may be indicated when FiO2 and EtO2 both increase in value and spontaneous respiration rate is lower than a threshold respiration rate, which indicates that the ventilator has been activated. Alternatively, case start may be detected when the standby setting of the anesthesia delivery machine is switched off. Therefore, case start may be detected responsive to an indication, from the monitoring parameters, that the patient has been connected to the anesthesia delivery machine and/or that the anesthesia delivery machine is activated in anticipation of anesthesia delivery to the patient.

At 708, method 700 includes applying a third subset of rules to the received monitoring parameters over the observation window in order to indicate that induction start is detected responsive to FiO2 not equaling EtO2 (e.g., divergence between FiO2 and EtO2) and spontaneous respiration rate becoming valid. Divergence between FiO2 and EtO2 (that may or may not persist since bag ventilation may eventually follow to intubate the patient manually) along with spontaneous respiration may indicate the consumption of oxygen by the patient because of high flow introduced in the breathing circuit of the anesthesia delivery machine by a clinician, for example. FiO2, EtO2, and spontaneous respiration rate may be parameters that are received from the anesthesia delivery machine. Further, any configuration (or at least most configurations) of the anesthesia delivery machine may output FiO2, EtO2, and spontaneous respiration rate. Accordingly, the third subset of rules may be applied to detect induction start regardless of the anesthesia delivery machine configuration and regardless of whether parameters are received from the patient monitor. Thus, all selected sets of rules may include the third subset of rules. Typically, a lag in detecting an IS event after case start is detected does not occur, but if there is significant delay, it could indicate delay in progress of the case due to unavailability of equipment and nurses/anesthesiologists, etc. (theatre inefficiency), which may be notified to the hospital administration.

At 710, a fourth subset of rules is applied to the received monitoring parameters (e.g., the monitoring parameters received over the observation window) in order to indicate that induction end is detected responsive to FiO2 and EtO2 diverging (e.g., changing from being equal to being unequal) during the observation window and staying unequal over the remaining observation window and spontaneous respiration rate being below the threshold respiration rate (or total respiration rate being greater than spontaneous respiration rate); or alternatively, mechanical ventilation being turned on (e.g., set mechanical ventilation being on) and spontaneous respiration rate not increasing (e.g., the last spontaneous respiration rate reading of the observation window minus the first spontaneous respiration rate of the observation window being less than zero). Thus, divergence of FiO2 and EtO2 without subsequent convergence in the observation window along with no spontaneous respiration (or spontaneous respiration being less than total respiration) is a signature that indicates induction end. All these phenomena happening together (e.g., convergence of FiO2 and EtO2 without spontaneous respiration) indicates that the patient is breathing/consuming oxygen without any interruptions (e.g., bag ventilation has probably ended). Not only this, this uninterrupted breathing is not spontaneous but mechanical on ventilator as can be observed from the spontaneous respiration rate, indicating that the patient is sedated or has minimal consciousness to facilitate tolerance of the insertion of endotracheal tube. In case both the above defined phenomena (stable divergence of FiO2 and EtO2 and vanishing spontaneous breathing) do not occur in the same window, the induction end signature will be missed. Hence, falling spontaneous respiration rate along with the set_mechanical_ventilation turning ON is used as a fallback signature. Similar to the third subset of rules, the fourth subset of rules may be applied to detect induction end regardless of the anesthesia delivery machine configuration and regardless of whether parameters are received from the patient monitor. Thus, all selected sets of rules may include the fourth subset of rules.

At 712, method 700 determines if the selected subset of rules includes a fifth subset of rules. As described above, the selected set of rules may include either a fifth subset, a sixth subset, or a seventh subset of rules that may be applied to detect emergence start, depending on the configuration of the anesthesia delivery machine. The fifth subset of rules may be included in the selected of rules when the anesthesia delivery machine has a first configuration wherein Set_FiO2 and/or Set_EtO2 are received and Set_insp_agent and/or Set_exp_agent are received. If the selected set of rules includes the fifth subset of rules, method 700 proceeds to 714 to apply the fifth subset of rules to the received monitoring parameters in order to indicate that emergence start is detected responsive to two of a first O2 signature, a flow signature, and a first agent signature being true; or alternatively, mechanical ventilation being set to off (and staying off through the observation window) and cardiac bypass mode (CBP) not being selected or being in the passive mode (no CBP). The first O2 signature may include set O2 (e.g., Set_FiO2 or Set_EtO2) rising and measured O2 (e.g., FiO2 or EtO2) rising with the set O2. Whether FiO2 or EtO2 is used in the first O2 signature may depend on the gas control mode of the anesthesia delivery machine, e.g., if the machine is in an expired gas or fresh gas control mode. The flow signature may include fresh gas flow rising to greater than a threshold flow rate (e.g., to equal to or greater than 4 L/min). The first agent signature may include set anesthetic agent dropping to 0. The set anesthetic agent may be Set_insp_agent or Set_exp_agent depending on the gas control mode of the anesthesia delivery machine. Further, to account for more than one anesthetic agent being delivered, the set anesthetic agent may equal a weighted sum of the anesthetic agents being delivered, such as set anesthetic agent=(set sevoflurane/2.05)+(set desflurane/6)+(set isoflurane/1.15). Rising O2 (which follows after a rise in the set_O2) and a rise in fresh gas flow may indicate that the clinician is attempting to oxygenate the patient and flush the anesthetic gases out of the circuit and bring the patient out of anesthesia (e.g., emergence start) so that the patient starts breathing spontaneously and the effect of sedation is gradually reduced.

If the selected set of rules does not include the fifth subset of rules, method 700 proceeds to 716 to determine if the selected set of rules includes a sixth subset of rules. The selected set of rules may include the sixth subset when the anesthesia delivery machine has a second configuration wherein Set_FiO2, Set_EtO2, Set_insp_agent, and Set_exp_agent are not received. If the selected set of rules does include the sixth subset of rules, method 700 proceeds to 718 to apply the sixth subset of rules to the received monitoring parameters, to detect emergence start responsive to two of a second O2 signature, the flow signature, and a second agent signature being true; or alternatively mechanical ventilation being set to off (and staying off) and CBP not being selected or being in passive mode (no CBP). The second O2 signature may include estimated set FiO2 rising. Estimated set FiO2 may be equal to (O2 flow+0.208*air flow)*100/fresh gas flow. The second agent signature may include inspired anesthetic agent dropping to approximately zero and crossover observed across inspired and expired anesthetic agents. The inspired anesthetic agent may be determined as inspired anesthetic agent=(inspired sevoflurane/2.05)+(inspired desflurane/6)+(inspired isoflurane/1.15).

If the selected set of rules does not include the sixth subset of rules, method 700 proceeds to 720 to apply a seventh subset of rules to the received monitoring parameters in order to detect emergence start responsive to two of the first O2 signature, the flow signature, and the second agent signature being true; or alternatively mechanical ventilation being set to off (and staying off) and CBP not being selected or being in passive mode (no CBP). The seventh subset of rules may be applied when the anesthesia delivery machine has a third configuration wherein Set_insp_agent and Set_exp_agent are not received.

At 722, method 700 includes determining if the selected set of rules includes an eighth subset of rules. The eighth subset of rules may be included in the subset of rules when the received monitoring parameters include one or more parameters from the patient monitor (e.g., SpO2, HR, PR). If the selected set of rules does include the eighth subset of rules, method 700 proceeds to 724 to apply the eighth subset of rules to the received monitoring parameters in order to detect case end responsive to FiO2 and EtO2 converging (e.g., differing by less than a threshold amount (e.g., less than 0.5) over the observation window), EtCO2 dropping to and staying at less than a threshold value (e.g., 0.2), and expired anesthetic agent dropping to and staying at 0 and not equaling inspired anesthetic agent (which may account for patient disconnections); or alternatively an anesthesia machine standby setting being on; or alternatively SpO2, HR, or PR changing from the valid range to the invalid range and staying in the invalid range over the observation window and EtCO2 being equal to or within range of zero (again to account for patient disconnections).

If the selected set of rules does not include the eighth subset (e.g., when the received monitoring parameters does not include one or more parameters from the patient monitor), method 700 proceeds to 726 to apply a ninth subset of rules to the received monitoring parameters in order to detect case end responsive to FiO2 and EtO2 converging (e.g., differing by less than the threshold amount over the observation window), EtCO2 dropping to and staying at less than the threshold value (e.g., 0.2), and expired anesthetic agent dropping to and staying at 0 and not equaling inspired anesthetic agent; or alternatively the anesthesia machine standby setting being on.

At 728, method 700 determines if an event is detected, wherein the event is one of case start, induction start, induction end, emergence start, and case end, by applying the selected set of rules to the received monitoring parameters as explained above. If an event is detected (e.g., case start is detected as explained above, induction start is detected above, induction end is detected as explained above, emergence start is detected as explained above, or case end is detected as explained above), method 700 proceeds to 730 to output an indication that an event was detected. The indication may include an identification of the event that was detected and a time stamp indicating the time at which the event was detected. The indication may be saved in memory (e.g., of computing system 120) and/or sent to one or more computing devices (e.g., first care provider device 134). The indication may be used to update a GUI, as explained above with respect to FIG. 6.

If an event is not detected (e.g., none of case start, induction start, induction end, emergence start, or case end is detected), method 700 proceeds to 732 to output an indication that no event was detected. The indication may be saved in memory (e.g., of computing system 120) and/or sent to one or more computing devices (e.g., first care provider device 134). When no event is detected, the indication may be used to maintain a current state of the GUI with respect to the patient, as explained above with respect to FIG. 6.

In some examples, two or more subsets of rules of the selected set of rules may be applied simultaneously to the received monitoring parameters, which may expedite the event detection. In such examples, an entirety of method 700 may be performed for each observation window of each patient, regardless of whether an event is detected or not. For example, method 700 may be performed to apply a selected set of rules to monitoring parameters received over an observation window for a patient and induction start may be detected. Despite induction start being detected, the remaining aspects of method 700 may still be carried out to determine if any other events are detected. In other examples, the subsets of rules of the selected set of rules may be applied serially (e.g., one after the other). In such examples, the next subset of rules may only be applied if an event was not detected in the current subset of rules. For example, the method may be terminated once an event is detected (e.g., once induction start is detected, any remaining subsets of rules not yet applied may not be applied), which may also expedite event detection by eliminating unnecessary continued event detection.

Thus, the systems and methods disclosed herein provide for anesthesia event detection and notification of patient anesthesia phase based on the anesthesia event detection. As described above with respect to FIG. 6 and shown in the examples illustrated in FIGS. 8-10 and described below, a GUI may be displayed that includes a first visual representation of a default or previously-determined phase of anesthesia delivery for a patient, such as in the form of a timeline. For example, the default phase may be "anesthesia delivery not started," which may be depicted via blank/white space on the timeline, or the previously-determined phase may be induction, which may be depicted via a first color or pattern on the timeline. A plurality of monitoring parameters of the patient may be received over an observation window, with at least a portion of the plurality of monitoring parameters being obtained from an anesthesia delivery machine. For example, all of the monitoring parameters may be obtained from the anesthesia delivery machine, or some of the monitoring parameters may be obtained from the anesthesia delivery machine while the remaining monitoring parameters may be obtained from a patient monitor. A selected set of rules may be applied to the plurality of monitoring parameters in order to identify whether an event signaling a change to a new phase of anesthesia delivery for the patient is detected, wherein the event is one of case start, induction start, induction end, emergence start, and case end. If the event is detected, the GUI may be updated to display a second visual representation of the new phase, such as changing a color or pattern on the timeline. Conversely, if the event is not detected, the first visual representation may be maintained on the GUI, for example, the timeline may continue to depict the color or pattern that indicates the default or previously-determined phase.

As explained previously, the monitoring parameters may or may not include parameters obtained from a patient monitor, and may or may not include parameters obtained with an anesthesia delivery machine having a given configuration. Thus, the monitoring parameters that are received may vary from patient to patient. To ensure accurate and rapid event detection regardless of the received monitoring parameters, different sets of rules may be applied to identify/ detect the event based on the monitoring parameters that are received. For example, an overall ruleset may be stored in memory that comprises nine subsets of rules. The selected set of rules may be assembled from the overall ruleset based on the received monitoring parameters. As an example, the overall ruleset may include a "best-case scenario" set of rules (also referred to as a first set of rules) that may be applied when the monitoring parameters include an expected set of monitoring parameters, and one or more other, second sets of rules that may be applied when the monitoring parameters do not include the expected set of monitoring parameters. When the monitoring parameters do include the expected set of monitoring parameters and the first set of rules is selected, applying the first set of rules may include applying a first subset of rules to determine if case start is detected; applying a third subset of rules to determine if induction start is detected; applying a fourth subset of rules to determine if induction end is detected; applying a fifth subset of rules, a sixth subset of rules, or a seventh subset of rules to determine if emergence start is detected; and applying an eighth subset of rules to determine if case end is detected. If an event is detected, the GUI may be updated such that second visual representation indicates that the patient is currently in a corresponding phase signaled by the event. For example, if case start is detected, the second visual representation may indicate that the patient is currently in case start; if induction start is detected, the second visual representation may indicate that the patient is currently in induction; and so forth, and if none of case start, induction start, induction end, emergence start, and case end is detected, the first visual representation may be maintained on the GUI.

In some examples, applying the first set of rules may include applying the first subset of rules to determine whether case start is detected may include determining that case start is detected responsive to oxygen saturation (SpO2), heart rate (HR), or pulse rate (PR) changing from an invalid range to a valid range; applying the third subset of rules to determine if induction start is detected may include determining that induction start is detected responsive to (a) and (b) being true, wherein (a) comprises fraction of inspired oxygen (FiO2) not being equal to end-tidal oxygen (EtO2) and (b) comprises spontaneous respiration rate changing from an invalid range to a valid range; applying the fourth subset of rules to determine if induction end is detected may include determining that induction end is detected responsive to (c) and (d) being true or (c) being true, wherein (c) comprises FiO2 and EtO2 changing from being equal to not being equal and staying not equal within the observation window, (d) comprises spontaneous respiration rate being below a threshold respiration rate or being below total respiration rate, and (c) comprises mechanical ventilation being set to on and a change in spontaneous respiration rate being less than 0; applying the fifth subset of rules to determine if emergence start is detected may include determining that emergence start is detected responsive to (f) or (g) being true, wherein (f) comprises two of a first O2 signature, a flow signature, and a first agent signature being true and (g) comprises mechanical ventilation being off and staying off through the observation window and cardiac bypass mode not being on or in passive mode, and wherein the first O2 signature comprises set O2 rising and measured O2 rising with the set O2, the flow signature comprises fresh gas flow rising to greater than a threshold flow rate, and the first agent signature comprises set anesthetic agent dropping to 0; and applying the eighth subset of rules to determine if case end is detected may include determining that case end is detected responsive to (h), (i), and (j) being true, or (k) being true, or (l) and (m) being true, wherein (h) comprises FiO2 and EtO2 differing by less than a threshold amount over the observation window, (i) comprises EtCO2 dropping to and staying less than a threshold EtCO2 value, (j) comprises expired anesthetic agent dropping to and staying at 0 and not equaling inspired anesthetic agent, (k) comprises an anesthesia machine standby setting being on, (l) comprises SpO2, HR, or PR changing from the valid range to the invalid range and staying in the invalid range over the observation window, and (m) comprises EtCO2 being equal to or within range of 0.

If the expected set of monitoring parameter is not received and a second set of rules is applied, applying the second set of rules to identify whether the event is detected may include applying a second subset of rules to determine if case start is detected; applying the third subset of rules to determine if induction start is detected; applying the fourth subset of rules to determine if induction end is detected; applying the fifth subset of rules, the sixth subset of rules, or the seventh subset of rules to determine if emergence start is detected; and applying a ninth subset of rules of the second set of rules to determine if case end is detected. Applying the second subset of rules to determine if case start is detected may include determining that case start is detected responsive to (n) or (o) being true, wherein (n) comprises FiO2 and EtO2 increasing together and spontaneous respiration rate being lower than the threshold respiration rate and (o) comprises the anesthesia machine standby setting being turned off; and applying the ninth subset of rules to determine if case end is detected may include determining that case end is detected responsive to (h), (i), and (j) being true, or (k) being true. It is to be appreciated that the second subset of rules and the ninth subset of rules may be applied when the monitoring parameters do not include parameters from the patient monitor.

In some examples, applying the sixth subset of rules or the seventh subset of rules may include determining that emergence start is detected responsive to (r) or (g) being true, wherein (r) comprises two of a second O2 signature, the flow signature, and a second agent signature being true, wherein the second O2 signature comprises estimated set FiO2 rising, and the second agent signature comprises inspired anesthetic agent dropping to approximately zero and crossover observed across inspired and expired anesthetic agents; or determining that emergence start is detected responsive to(s) or (g) being true, wherein(s) comprises two of the first O2 signature, the flow signature, and the second agent signature being true. The sixth or seventh subset of rules may be applied when the anesthesia delivery machine is of a particular configuration (e.g., non-premium, legacy) that does not output certain monitoring parameters, such as set FiO2/set EtO2. For example, when the plurality of monitoring parameters includes set O2 and set anesthetic agent concentration, the fifth subset of rules may be applied to identify whether emergence start is detected; when the plurality of monitoring parameters does not include the set O2 and the set anesthetic agent concentration, the sixth subset of rules may be applied to identify whether emergence start is detected; and when the plurality of monitoring parameters includes the set O2 but not the set anesthetic agent concentration, the seventh subset of rules may be applied to identify whether emergence start is detected.

Further, as explained above with respect to FIG. 5, some of the received monitoring parameters may be received in a standardized format (e.g., at a first, higher frequency), while other monitoring parameters may be received in a non-standardized format (e.g., at a second, lower frequency). The monitoring parameters received in the non-standardized format may be converted to the standardized format (e.g., to the first frequency via interpolation with the prior 30 seconds' worth of values for that monitoring parameter) before the monitoring parameters are analyzed to detect an event as described above. In doing so, various different monitoring parameters indicative of anesthesia delivery steps/actions may be analyzed in the same standardized format, regardless of the format in which the monitoring parameters were received.

FIG. 8 shows an example GUI 800 in a first state 801. GUI 800 may be displayed on a display device (e.g., of first care provider device 134) and may be generated and updated accordingly to method 600 of FIG. 6 based on anesthesia delivery event detections according to methods 500 and 700 of FIGS. 5 and 7A and 7B. GUI 800 may include an OR status panel 802 that includes a plurality of display elements that provide a summary of current phases for all of a plurality of patients undergoing anesthesia delivery at a specific facility, ward, or unit (e.g., the operating rooms of a hospital). The plurality of display elements may include a first display element 804 that indicates the number of patients undergoing induction, a second display element 806 that indicates the number of patients undergoing maintenance, and a third display element 808 that indicates the number of patients undergoing emergence. Additional display elements may be included in the OR status panel, such as a fourth display panel that indicates the total number of patients in a monitoring mode (e.g., where the anesthesia delivery machine has been switched to a "monitoring only mode") and/or the number of open operating rooms.

GUI 800 further includes a plurality of anesthesia delivery timelines 810. Each timeline of the plurality of timelines 810 depicts anesthesia delivery phase as a function of time for a respective patient of the plurality of patients. In some examples, the amount of time that is shown on the GUI 800 may be adjusted by a user by selecting a time element. As shown in FIG. 8, a user has selected to view the past three hours of time and the timelines are adjusted to show three hours of time. The user may instead select to see the past hour of time, the past six hours of time, the past day (e.g., 12 or 24 hours), or another suitable amount, and the timelines may be expanded or contracted accordingly.

As an example, a timeline 812 is depicted that shows anesthesia delivery phase as a function of time for the patient(s) within a selected operating room, in this example OR4. The timeline 812 may visually depict current anesthesia phase as a color-coded bar. For example, induction is shown as a first color at region 814 and maintenance is shown as a second color at region 816. Induction (e.g., region 814) may commence at the time specified in a first indication that induction start was detected for the patient. Maintenance may commence at the time specified in a second indication that induction end was detected for the patient. The first and second indications may be generated as described above with respect to FIGS. 5-7B. Thus, when the second indication is received (indicating detection of an event signaling a change to a new phase), the timeline 812 may be adjusted to add the new phase (e.g., changing from the first color to the second color). After the second indication is received, additional indications received may not identify an event and thus the timeline 812 may be maintained (e.g., the region 816 may extend in time but stay in the second color).

In some examples, GUI 800 may further include a pop-up panel 818 that may be displayed in response to a hover input being received over a selected phase of a selected timeline (e.g., an input being received to region 814 of timeline 812). The pop-up panel 818 may include additional information about the selected phase, such as the phase name (e.g., induction), duration of the phase, start time of the phase, and end time of the phase. In the example shown, the pop-up panel 818 indicates that induction started at 9:25, ended at 9:35, and lasted 10 minutes.

GUI 800 is shown in a second state 901 in FIG. 9. In the second state, a different hover input has been received (e.g., over region 816 of timeline 812), resulting in another pop-up panel 902 being displayed that identifies maintenance phase started at 9:35, has yet to end (e.g., is ongoing), and has a current duration of 41 minutes.

GUI 800 is shown in a third state 1001 in FIG. 10. In the third state, a different hover input has been received (e.g., over a completed case region 1004 of timeline 812), resulting in another pop-up panel 1002 being displayed that identifies the prior case occurring in OR4 (e.g., a prior patient) has completed, with a duration of 1 hour 7 minutes, starting at 8:08 and ending at 9:15. The completed case may be identified with a particular color, such as gray.

While not shown in the GUI of FIGS. 8-10, in some examples, various notifications may be provided via the GUI, such as notifications that indicate a particular phase of anesthesia delivery for a patient has extended beyond a threshold duration. For example, if case start for the patient lasts longer than a first threshold duration (e.g., ten minutes), a first notification may be displayed to alert users of the extended case start phase, as the extended case start phase may indicate a delay in progressing the patient to reception of anesthesia due to unavailability of equipment and/or personnel. As another example, if emergence for the patient lasts longer than a second threshold duration (e.g., 20 minutes), a second notification may be displayed to alert uses of the extended emergence, which may indicate that the patient is exhibiting deep anesthesia and/or that logistical issues (e.g., lack of beds or personnel) are hindering movement of the patient out of the operating room. By automatically determining anesthesia phase for each of a plurality of patients, visually indicating the current phase for each patient via the GUI, and notifying when a current phase has extended beyond a threshold duration, a user may be apprised of the current status and/or any issues arising with anesthesia delivery for each patient without having to be in the room with the patient, without having to directly communicate with any clinicians attending to the patient, and without having to access an electronic medical records or other data sources pertaining to the patients. In doing so, efficiency of the overall system may be improved by reducing undue delays between patients in the operating rooms, reducing user interaction with patient data/monitoring parameters in an attempt to ascertain the current phase of anesthesia delivery for one or more or each patient in the medical facility, and the like.

In still further examples, one or more notifications may be displayed when a pause or interruption in reception of one or more monitoring parameters for a patient occurs. As explained above, the events that signal a change to a new phase of anesthesia delivery may only occur during one observation window, or over a few observation windows. As such, the majority of indications that are generated may indicate that no event is detected and the GUI may continue to maintain the previously-determined anesthesia phase. However, if one or more monitoring parameters for a patient are not received for a period of time (e.g., the anesthesia delivery machine for that patient loses connection to the network), the GUI may continue to indicate that the patient is in the previous anesthesia phase even if the patient has transitioned to a new phase, as the event signaling the change to the new phase may be missed due to the monitoring parameters not being received during the event. As such, if one or more monitoring parameters are not received over the observation window or over two or more consecutive observation windows, an indication may be generated that the event detection (or lack thereof) is not reliable and/or rather than sending an indication of a detected event or an indication that no event was detected, an indication may be sent that indicates insufficient monitoring parameter data was received to determine if an event was detected or not. In such examples, the GUI may be updated to reflect the unreliable or undeterminable event/no event detection.

A technical effect of identifying, by applying a selected set of rules to a plurality of patient monitoring parameters, whether an event signaling a change to a new phase of anesthesia delivery for a patient is detected, and if the event is detected, updating a GUI to display a visual representation of the new phase, is that anesthesia phase may be detected automatically using parameters from the anesthesia delivery machine without requiring separate/dedicated monitoring devices such as EEGs, which may increase processing efficiency by utilizing parameters already available/being analyzed and without having to process and analyze data from the separate/dedicated monitoring devices. The anesthesia phase may be displayed or otherwise indicated to one or more users, such as administrators or clinicians, which may facilitate enhanced patient care and operational efficiency. By utilizing the event detection described herein, and particularly by selecting a set of rules to apply for detecting the events based on received monitoring parameters, events signaling a change to a new phase of anesthesia delivery may be detected as quickly as the available monitoring parameters allow without having to know the specific configuration of the particular anesthesia delivery machine being used. Further, by using a sliding observation window of monitoring parameters (that is the same duration for each parameter and each observation window) of a suitable duration (e.g., one minute), slow/delayed parameters may still be detected while allowing for rapid detection of an event.

The disclosure also provides support for a system, comprising: one or more processors, and memory storing instructions executable by the one or more processors to: output, for display on a display device, a graphical user interface (GUI) including a first visual representation of a default or previously-determined phase of anesthesia delivery for a patient, receive a plurality of monitoring parameters of the patient over an observation window, at least a portion of the plurality of monitoring parameters obtained from an anesthesia delivery machine, identify, by applying a selected set of rules to the plurality of monitoring parameters, whether an event signaling a change to a new phase of anesthesia delivery for the patient is detected, wherein the event is one of case start, induction start, induction end, emergence start, and case end, based on the event being detected, update the GUI to display a second visual representation of the new phase, and based on the event not being detected, maintain the first visual representation on the GUI. In a first example of the system, the instructions are executable to: determine whether the plurality of monitoring parameters includes an expected set of monitoring parameters, based on the plurality of monitoring parameters including the expected set of monitoring parameters, select a first set of rules and apply the first set of rules to identify whether the event is detected, and based on the plurality of monitoring parameters not including the expected set of monitoring parameters, select a second set of rules and apply the second set of rules to identify whether the event is detected. In a second example of the system, optionally including the first example, executing the instructions to select the first set of rules and apply the first set of rules to identify whether the event is detected comprises: applying a first subset of rules to determine if case start is detected, applying a third subset of rules to determine if induction start is detected, applying a fourth subset of rules to determine if induction end is detected, applying a fifth subset of rules, a sixth subset of rules, or a seventh subset of rules to determine if emergence start is detected, applying an eighth subset of rules to determine if case end is detected, if case start is detected, updating the GUI to display the second visual representation, the second visual representation indicating that the patient is currently in case start, if induction start is detected, updating the GUI to display the second visual representation, the second visual representation indicating that the patient is currently in induction, if induction end is detected, updating the GUI to display the second visual representation, the second visual representation indicating that the patient is currently in maintenance, if emergence start is detected, updating the GUI to display the second visual representation, the second visual representation indicating that the patient is currently in emergence, if case end is detected, updating the GUI to display the second visual representation, the second visual representation indicating that the patient is currently in case end, and if none of case start, induction start, induction end, emergence start, and case end is detected, maintaining the first visual representation on the GUI. In a third example of the system, optionally including one or both of the first and second examples, executing the instructions to apply the fifth subset of rules, the sixth subset of rules, or the seventh subset of rules to determine if emergence start is detected comprises applying the fifth subset of rules, and wherein: applying the first subset of rules to determine if case start is detected comprises determining that case start is detected responsive to oxygen saturation (SpO2), heart rate (HR), or pulse rate (PR) changing from an invalid range to a valid range, applying the third subset of rules to determine if induction start is detected comprises determining that induction start is detected responsive to (a) and (b) being true, wherein (a) comprises fraction of inspired oxygen (FiO2) not being equal to end-tidal oxygen (EtO2) and (b) comprises spontaneous respiration rate changing from an invalid range to a valid range, applying the fourth subset of rules to determine if induction end is detected comprises determining that induction end is detected responsive to (c) and (d) being true or (e) being true, wherein (c) comprises FiO2 and EtO2 changing from being equal to not being equal and staying not equal within the observation window, (d) comprises spontaneous respiration rate being below a threshold respiration rate or being below a total respiration rate, and (c) comprises mechanical ventilation being set to on and a change in spontaneous respiration rate being less than 0, applying the fifth subset of rules to determine if emergence start is detected comprises determining that emergence start is detected responsive to (f) or (g) being true, wherein (f) comprises two of a first O2 signature, a flow signature, and a first agent signature being true and (g) comprises mechanical ventilation being off and staying off through the observation window and cardiac bypass mode not being on or in passive mode, and wherein the first O2 signature comprises set O2 rising and measured O2 rising with the set O2, the flow signature comprises fresh gas flow rising to greater than a threshold flow rate, and the first agent signature comprises set anesthetic agent dropping to 0, and applying the eighth subset of rules to determine if case end is detected comprises determining that case end is detected responsive to (h), (i), and (j) being true, or (k) being true, or (l) and (m) being true, wherein (h) comprises FiO2 and EtO2 differing by less than a threshold amount over the observation window, (i) comprises EtCO2 dropping to and staying less than a threshold EtCO2 value, (j) comprises expired anesthetic agent dropping to and staying at 0 and not equaling inspired anesthetic agent, (k) comprises an anesthesia machine standby setting being on, (l) comprises SpO2, HR, or PR changing from the valid range to the invalid range and staying in the invalid range over the observation window, and (m) comprises EtCO2 being equal to or within range of 0. In a fourth example of the system, optionally including one or more or each of the first through third examples, executing the instructions to select the second set of rules and apply the second set of rules to identify whether the event is detected comprises: applying a second subset of rules to determine if case start is detected, applying the third subset of rules to determine if induction start is detected, applying the fourth subset of rules to determine if induction end is detected, applying the fifth subset of rules, the sixth subset of rules, or the seventh subset of rules to determine if emergence start is detected, applying a ninth subset of rules of the second set of rules to determine if case end is detected, based on case start being detected, updating the GUI to display the second visual representation, the second visual representation indicating that the patient is currently in case start, based on induction start being detected, updating the GUI to display the second visual representation, the second visual representation indicating that the patient is currently in induction, based on induction end being detected, updating the GUI to display the second visual representation, the second visual representation indicating that the patient is currently in maintenance, based on emergence start being detected, updating the GUI to display the second visual representation, the second visual representation indicating that the patient is currently in emergence, based on case end being detected, updating the GUI to display the second visual representation, the second visual representation indicating that the patient is currently in case end, and based on none of case start, induction start, induction end, emergence start, and case end being detected, maintaining the first visual representation on the GUI. In a fifth example of the system, optionally including one or more or each of the first through fourth examples, executing the instructions to apply the second subset of rules to determine whether case start is detected comprises determining that case start is detected responsive to (n) or (o) being true, wherein (n) comprises FiO2 and EtO2 increasing together and spontaneous respiration rate being lower than the threshold respiration rate and (o) comprises the anesthesia machine standby setting being turned off, and applying the ninth subset of rules to determine whether case end is detected comprises determining that case end is detected responsive to (h), (i), and (j) being true, or (k) being true. In a sixth example of the system, optionally including one or more or each of the first through fifth examples, executing the instructions to apply the fifth subset of rules, the sixth subset of rules, or the seventh subset of rules to determine whether emergence start is detected comprises applying the sixth subset of rules or the seventh subset of rules, wherein executing the instructions to apply the sixth subset of rules or the seventh subset of rules comprises: determining that emergence start is detected responsive to (r) or (g) being true, wherein (r) comprises two of a second O2 signature, the flow signature, and a second agent signature being true, wherein the second O2 signature comprises estimated set FiO2 rising, and the second agent signature comprises inspired anesthetic agent dropping to approximately zero and crossover observed across inspired and expired anesthetic agents, or determining that emergence start is detected responsive to(s) or (g) being true, wherein(s) comprises two of the first O2 signature, the flow signature, and the second agent signature being true. In a seventh example of the system, optionally including one or more or each of the first through sixth examples, the first set of rules and the second set of rules are each stored in the memory. In an eighth example of the system, optionally including one or more or each of the first through seventh examples, the observation window is a window of time over which the plurality of monitoring parameters is received and processed, and wherein the instructions are executable to: based on the plurality of monitoring parameters including the expected set of monitoring parameters, apply the first set of rules to the plurality of monitoring parameters received over the observation window, and based on the plurality of monitoring parameters not including the expected set of monitoring parameters, apply the second set of rules to the plurality of monitoring parameters received over the observation window.

The disclosure also provides support for a system, comprising: one or more processors, and memory storing instructions executable by the one or more processors to: output, for display on a display device, a graphical user interface (GUI) including a plurality of timelines of anesthesia delivery phases, each timeline depicting anesthesia delivery phase as a function of time for a respective patient of a plurality of patients, for a first patient of the plurality of patients, receive a plurality of monitoring parameters of the first patient over an observation window, at least a portion of the plurality of monitoring parameters obtained from an anesthesia delivery machine, identify, in real-time and without knowing a current or prior phase of anesthesia delivery for the first patient, whether an event signaling a change to a new phase of anesthesia delivery for the first patient is detected based on the plurality of monitoring parameters, wherein the event is one of case start, induction start, induction end, emergence start, and case end, based on the event being detected, update the GUI to add the new phase to a first timeline of the plurality of timelines, the first timeline representing anesthesia delivery phases for the first patient, and based on the event not being detected, maintain the first timeline for the first patient on the GUI. In a first example of the system, the event is induction start and the GUI is updated to start the first timeline and indicate induction has started via a first color of the first timeline starting when induction start is detected. In a second example of the system, optionally including the first example, the event is induction end and the GUI is updated to indicate maintenance has started by changing the first timeline from a first color to a second color starting when induction end is detected. In a third example of the system, optionally including one or both of the first and second examples, the event is emergence start and the GUI is updated to indicate emergence has started by changing the first timeline from a second color to a third color starting when emergence start is detected. In a fourth example of the system, optionally including one or more or each of the first through third examples, the instructions are further executable to display, on the GUI, a pop-up panel in response to a hover input being received over a selected phase of the first timeline, the pop-up panel including additional information about the selected phase. In a fifth example of the system, optionally including one or more or each of the first through fourth examples, the GUI further includes an operating room status panel including a summary of current phases for all of the plurality of patients. In a sixth example of the system, optionally including one or more or each of the first through fifth examples, the memory stores an overall ruleset for detecting each of case start, induction start, induction end, emergence start, and case end, the overall ruleset including a first subset of rules and a second subset of rules for detecting case start, a third subset of rules for detecting induction start, a fourth subset of rules for detecting induction end, a fifth subset of rules, a sixth subset of rules, and a seventh subset of rules for detecting emergence start, and an eighth subset of rules and a ninth subset of rules for detecting case end. In a seventh example of the system, optionally including one or more or each of the first through sixth examples, executing the instructions to identify whether the event is detected based on the plurality of monitoring parameters comprises: based on the plurality of monitoring parameters being received from both the anesthesia delivery machine and a patient monitor, selecting the first subset of rules and the eighth subset of rules, and applying the first subset of rules to identify whether case start is detected and applying the eighth subset of rules to identify whether case end is detected, and based on the plurality of monitoring parameters being received from only the anesthesia delivery machine, selecting the second subset of rules and the ninth subset of rules, and applying the second subset of rules to identify whether case start is detected and applying the ninth subset of rules to identify whether case end is detected. In an eighth example of the system, optionally including one or more or each of the first through seventh examples, executing the instructions to identify whether the event is detected based on the plurality of monitoring parameters comprises: based on the plurality of monitoring parameters including set O2 and set anesthetic agent concentration, selecting the fifth subset of rules and applying the fifth subset of rules to identify whether emergence start is detected, based on the plurality of monitoring parameters not including the set O2 and the set anesthetic agent concentration, selecting the sixth subset of rules and applying the sixth subset of rules to identify whether emergence start is detected, and based on the plurality of monitoring parameters including the set O2 but not the set anesthetic agent concentration, selecting the seventh subset of rules and applying the seventh subset of rules to identify whether emergence start is detected.

The disclosure also provides support for a system, comprising: one or more processors, and memory storing instructions executable by the one or more processors to:

receive one or more first patient monitoring parameters for a first patient in a standardized format, receive a one or more second patient monitoring parameters for the first patient in a non-standardized format, convert the one or more second patient monitoring parameters from the non-standardized format into the standardized format, identify, in real-time and without knowing a current or prior phase of anesthesia delivery for the first patient, that an event signaling a change to a new phase of anesthesia delivery for the first patient has occurred based on the one or more first patient monitoring parameters and the one or more second patient monitoring parameters in the standardized format, wherein the event is one of case start, induction start, induction end, emergence start, and case end, automatically generate an indication that the change to the new phase for the first patient has occurred, and update a graphical user interface based on the indication. In a first example of the system, the instructions are executable to identify that the event signaling a change to a new phase of anesthesia delivery for the first patient has occurred based on the one or more first patient monitoring parameters and the one or more second patient monitoring parameters in the standardized format comprises applying a selected set of rules to the one or more first patient monitoring parameters and the one or more second patient monitoring parameters in the standardized format, wherein the selected set of rules includes a plurality of subsets of rules, and wherein at least one subset of rules of the plurality of subsets of rules is selected based on the one or more first patient monitoring parameters and the one or more second patient monitoring parameters.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A system, comprising:
one or more processors; and
memory storing instructions executable by the one or more processors to:
output, for display on a display device, a graphical user interface (GUI) including a first visual representation of a default or previously-determined phase of anesthesia delivery for a patient;

receive a plurality of monitoring parameters of the patient over an observation window, at least a portion of the plurality of monitoring parameters obtained from an anesthesia delivery machine;

identify, by applying a selected set of rules to the plurality of monitoring parameters, whether an event signaling a change to a new phase of anesthesia delivery for the patient is detected, wherein the event is one of case start, induction start, induction end, emergence start, and case end;

based on the event being detected, update the GUI to display a second visual representation of the new phase; and based on the event not being detected, maintain the first visual representation on the GUI, wherein the selected set of rules includes a plurality of subsets of rules, with each respective subset of rules configured to detect a respective one of case start, induction start, induction end, emergence start, and case end, and wherein each subset of rules is applied to the plurality of monitoring parameters regardless of the default or previously-determined phase of anesthesia delivery.

2. The system of claim 1, wherein the instructions are executable to:

determine whether the plurality of monitoring parameters includes an expected set of monitoring parameters;

based on the plurality of monitoring parameters including the expected set of monitoring parameters, select a first set of rules and apply the first set of rules to identify whether the event is detected, the first set of rules including a first plurality of subsets of rules; and based on the plurality of monitoring parameters not including the expected set of monitoring parameters, select a second set of rules and apply the second set of rules to identify whether the event is detected, the second set of rules including a second plurality of subsets of rules.

3. The system of claim 2, wherein executing the instructions to select the first set of rules and apply the first set of rules to identify whether the event is detected comprises:

applying a first subset of rules to determine if case start is detected;

applying a third subset of rules to determine if induction start is detected;

applying a fourth subset of rules to determine if induction end is detected;

applying a fifth subset of rules, a sixth subset of rules, or a seventh subset of rules to determine if emergence start is detected;

applying an eighth subset of rules to determine if case end is detected;

if case start is detected, updating the GUI to display the second visual representation, the second visual representation indicating that the patient is currently in case start;

if induction start is detected, updating the GUI to display the second visual representation, the second visual representation indicating that the patient is currently in induction;

if induction end is detected, updating the GUI to display the second visual representation, the second visual representation indicating that the patient is currently in maintenance;

if emergence start is detected, updating the GUI to display the second visual representation, the second visual representation indicating that the patient is currently in emergence;

if case end is detected, updating the GUI to display the second visual representation, the second visual representation indicating that the patient is currently in case end; and if none of case start, induction start, induction end, emergence start, and case end is detected, maintaining the first visual representation on the GUI.

4. The system of claim 3, wherein executing the instructions to apply the fifth subset of rules, the sixth subset of rules, or the seventh subset of rules to determine if emergence start is detected comprises applying the fifth subset of rules, and wherein:

applying the first subset of rules to determine if case start is detected comprises determining that case start is detected responsive to oxygen saturation (SpO2), heart rate (HR), or pulse rate (PR) changing from an invalid range to a valid range;

applying the third subset of rules to determine if induction start is detected comprises determining that induction start is detected responsive to (a) and (b) being true, wherein (a) comprises fraction of inspired oxygen (FiO2) not being equal to end-tidal oxygen (EtO2) and (b) comprises spontaneous respiration rate changing from an invalid range to a valid range;

applying the fourth subset of rules to determine if induction end is detected comprises determining that induction end is detected responsive to (c) and (d) being true or (e) being true, wherein (c) comprises FiO2 and EtO2 changing from being equal to not being equal and staying not equal within the observation window, (d) comprises spontaneous respiration rate being below a threshold respiration rate or being below a total respiration rate, and (e) comprises mechanical ventilation being set to on and a change in spontaneous respiration rate being less than 0;

applying the fifth subset of rules to determine if emergence start is detected comprises determining that emergence start is detected responsive to (f) or (g) being true, wherein (f) comprises two of a first O2 signature, a flow signature, and a first agent signature being true and (g) comprises mechanical ventilation being off and staying off through the observation window and cardiac bypass mode not being on or in passive mode, and wherein the first O2 signature comprises set O2 rising and measured O2 rising with the set O2, the flow signature comprises fresh gas flow rising to greater than a threshold flow rate, and the first agent signature comprises set anesthetic agent dropping to 0; and applying the eighth subset of rules to determine if case end is detected comprises determining that case end is detected responsive to (h), (i), and (j) being true, or (k) being true, or (l) and (m) being true, wherein (h) comprises FiO2 and EtO2 differing by less than a threshold amount over the observation window, (i) comprises EtCO2 dropping to and staying less than a threshold EtCO2 value, (j) comprises expired anesthetic agent dropping to and staying at 0 and not equaling inspired anesthetic agent, (k) comprises an anesthesia machine standby setting being on, (l) comprises SpO2, HR, or PR changing from the valid range to the invalid range and staying in the invalid range over the observation window, and (m) comprises EtCO2 being equal to or within range of 0.

5. The system of claim 4, wherein executing the instructions to select the second set of rules and apply the second set of rules to identify whether the event is detected comprises:

applying a second subset of rules to determine if case start is detected;

applying the third subset of rules to determine if induction start is detected;

applying the fourth subset of rules to determine if induction end is detected;

applying the fifth subset of rules, the sixth subset of rules, or the seventh subset of rules to determine if emergence start is detected;

applying a ninth subset of rules of the second set of rules to determine if case end is detected;

based on case start being detected, updating the GUI to display the second visual representation, the second visual representation indicating that the patient is currently in case start;

based on induction start being detected, updating the GUI to display the second visual representation, the second visual representation indicating that the patient is currently in induction;

based on induction end being detected, updating the GUI to display the second visual representation, the second visual representation indicating that the patient is currently in maintenance;

based on emergence start being detected, updating the GUI to display the second visual representation, the second visual representation indicating that the patient is currently in emergence;

based on case end being detected, updating the GUI to display the second visual representation, the second visual representation indicating that the patient is currently in case end; and based on none of case start, induction start, induction end, emergence start, and case end being detected, maintaining the first visual representation on the GUI.

6. The system of claim 5, wherein:

executing the instructions to apply the second subset of rules to determine whether case start is detected comprises determining that case start is detected responsive to (n) or (o) being true, wherein (n) comprises FiO2 and EtO2 increasing together and spontaneous respiration rate being lower than the threshold respiration rate and (o) comprises the anesthesia machine standby setting being turned off; and applying the ninth subset of rules to determine whether case end is detected comprises determining that case end is detected responsive to (h), (i), and (j) being true, or (k) being true.

7. The system of claim 5, wherein executing the instructions to apply the fifth subset of rules, the sixth subset of rules, or the seventh subset of rules to determine whether emergence start is detected comprises applying the sixth subset of rules or the seventh subset of rules, wherein executing the instructions to apply the sixth subset of rules or the seventh subset of rules comprises:

determining that emergence start is detected responsive to (r) or (g) being true, wherein (r) comprises two of a second O2 signature, the flow signature, and a second agent signature being true, wherein the second O2 signature comprises estimated set FiO2 rising, and the second agent signature comprises inspired anesthetic agent dropping to approximately zero and crossover observed across inspired and expired anesthetic agents; or determining that emergence start is detected responsive to(s) or (g) being true, wherein(s) comprises two of the first O2 signature, the flow signature, and the second agent signature being true.

8. The system of claim 2, wherein the first set of rules and the second set of rules are each stored in the memory.

9. The system of claim 2, wherein the observation window is a window of time over which the plurality of monitoring parameters is received and processed, and wherein the instructions are executable to:

based on the plurality of monitoring parameters including the expected set of monitoring parameters, apply the first set of rules to the plurality of monitoring parameters received over the observation window, and based on the plurality of monitoring parameters not including the expected set of monitoring parameters, apply the second set of rules to the plurality of monitoring parameters received over the observation window.

10. A system, comprising:

one or more processors; and memory storing instructions executable by the one or more processors to:

output, for display on a display device, a graphical user interface (GUI) including a plurality of timelines of anesthesia delivery phases, each timeline depicting anesthesia delivery phase as a function of time for a respective patient of a plurality of patients;

for a first patient of the plurality of patients, receive a plurality of monitoring parameters of the first patient over an observation window, at least a portion of the plurality of monitoring parameters obtained from an anesthesia delivery machine;

identify, in real-time and without knowing a current or prior phase of anesthesia delivery for the first patient, whether an event signaling a change to a new phase of anesthesia delivery for the first patient is detected based on the plurality of monitoring parameters, wherein the event is one of case start, induction start, induction end, emergence start, and case end;

based on the event being detected, update the GUI to add the new phase to a first timeline of the plurality of timelines, the first timeline representing anesthesia delivery phases for the first patient; and based on the event not being detected, maintain the first timeline for the first patient on the GUI, wherein the memory stores an overall ruleset for detecting each of case start, induction start, induction end, emergence start, and case end, the overall ruleset including a first subset of rules and a second subset of rules for detecting case start, a third subset of rules for detecting induction start, a fourth subset of rules for detecting induction end, a fifth subset of rules, a sixth subset of rules, and a seventh subset of rules for detecting emergence start, and an eighth subset of rules and a ninth subset of rules for detecting case end.

11. The system of claim 10, wherein the event is induction start and the GUI is updated to start the first timeline and indicate induction has started via a first color of the first timeline starting when induction start is detected.

12. The system of claim 10, wherein the event is induction end and the GUI is updated to indicate maintenance has started by changing the first timeline from a first color to a second color starting when induction end is detected.

13. The system of claim 10, wherein the event is emergence start and the GUI is updated to indicate emergence has started by changing the first timeline from a second color to a third color starting when emergence start is detected.

14. The system of claim 10, wherein the instructions are further executable to display, on the GUI, a pop-up panel in response to a hover input being received over a selected phase of the first timeline, the pop-up panel including additional information about the selected phase.

15. The system of claim 10, wherein the GUI further includes an operating room status panel including a summary of current phases for all of the plurality of patients.

16. The system of claim 10, wherein executing the instructions to identify whether the event is detected based on the plurality of monitoring parameters comprises:

based on the plurality of monitoring parameters being received from both the anesthesia delivery machine and a patient monitor, selecting the first subset of rules and the eighth subset of rules, and applying the first subset of rules to identify whether case start is detected and applying the eighth subset of rules to identify whether case end is detected; and based on the plurality of monitoring parameters being received from only the anesthesia delivery machine, selecting the second subset of rules and the ninth subset of rules, and applying the second subset of rules to identify whether case start is detected and applying the ninth subset of rules to identify whether case end is detected.

17. The system of claim 10, wherein executing the instructions to identify whether the event is detected based on the plurality of monitoring parameters comprises:

based on the plurality of monitoring parameters including set O2 and set anesthetic agent concentration, selecting the fifth subset of rules and applying the fifth subset of rules to identify whether emergence start is detected;

based on the plurality of monitoring parameters not including the set O2 and the set anesthetic agent concentration, selecting the sixth subset of rules and applying the sixth subset of rules to identify whether emergence start is detected; and based on the plurality of monitoring parameters including the set O2 but not the set anesthetic agent concentration, selecting the seventh subset of rules and applying the seventh subset of rules to identify whether emergence start is detected.

18. A system, comprising:
one or more processors; and
memory storing instructions executable by the one or more processors to:

receive one or more first patient monitoring parameters for a first patient in a standardized format;

receive a one or more second patient monitoring parameters for the first patient in a non-standardized format;

convert the one or more second patient monitoring parameters from the non-standardized format into the standardized format;

identify, in real-time and without knowing a current or prior phase of anesthesia delivery for the first patient, that an event signaling a change to a new phase of anesthesia delivery for the first patient has occurred based on the one or more first patient monitoring parameters and the one or more second patient monitoring parameters in the standardized format, wherein the event is one of case start, induction start, induction end, emergence start, and case end;

automatically generate an indication that the change to the new phase for the first patient has occurred; and update a graphical user interface based on the indication.

19. The system of claim 18, wherein the instructions are executable to identify that the event signaling a change to a new phase of anesthesia delivery for the first patient has occurred based on the one or more first patient monitoring parameters and the one or more second patient monitoring parameters in the standardized format comprises applying a selected set of rules to the one or more first patient monitoring parameters and the one or more second patient monitoring parameters in the standardized format, wherein the selected set of rules includes a plurality of subsets of rules, and wherein at least one subset of rules of the plurality of subsets of rules is selected based on the one or more first patient monitoring parameters and the one or more second patient monitoring parameters.

* * * * *